US008622213B2

(12) United States Patent
Lynn et al.

(10) Patent No.: US 8,622,213 B2
(45) Date of Patent: Jan. 7, 2014

(54) CONTAINERS AND COMPONENTS THEREOF FOR USE IN THE MEDICAL INDUSTRY AND METHODS TO MANUFACTURE THE SAME

(75) Inventors: Daniel Lynn, Spring Grove, IL (US); Richard L. West, Lake Villa, IL (US); Tat Mui, Chicago, IL (US); Mark B. Jones, Libertyville, IL (US)

(73) Assignee: Fenwal, Inc., Lake Zurich, IL (US)

( * ) Notice: Subject to any disclaimer, the term of this patent is extended or adjusted under 35 U.S.C. 154(b) by 706 days.

(21) Appl. No.: 12/785,284

(22) Filed: May 21, 2010

(65) Prior Publication Data

US 2010/0294693 A1 Nov. 25, 2010

Related U.S. Application Data

(60) Provisional application No. 61/240,022, filed on Sep. 4, 2009, provisional application No. 61/229,998, filed on Jul. 30, 2009, provisional application No. 61/180,544, filed on May 22, 2009.

(51) Int. Cl.
*A61B 17/06* (2006.01)

(52) U.S. Cl.
USPC .............. 206/438; 220/270; 604/19; 604/408

(58) Field of Classification Search
USPC ............. 206/438, 484; 604/19, 408; 220/270, 220/676
See application file for complete search history.

(56) References Cited

U.S. PATENT DOCUMENTS

| | | | | |
|---|---|---|---|---|
| 3,509,879 | A | 5/1970 | Bathish et al. | |
| 3,583,460 | A | 6/1971 | Riverside et al. | |
| 3,788,374 | A | 1/1974 | Saijo | |
| 4,119,128 | A | 10/1978 | Bishop | |
| 4,183,434 | A * | 1/1980 | Watt | 206/438 |
| 4,294,574 | A * | 10/1981 | Bayham | 493/213 |
| 4,917,684 | A | 4/1990 | Yasumura | |
| 4,921,137 | A | 5/1990 | Heijenga | |
| 5,251,982 | A | 10/1993 | Stenstrom et al. | |
| 5,312,189 | A | 5/1994 | Aeschbach et al. | |
| 5,366,296 | A | 11/1994 | Stenstrom et al. | |
| 5,391,163 | A * | 2/1995 | Christine et al. | 604/408 |
| 6,076,664 | A | 6/2000 | Yeager | |
| 6,165,161 | A * | 12/2000 | York et al. | 604/408 |
| 7,360,807 | B2 * | 4/2008 | Graves | 292/307 R |

* cited by examiner

*Primary Examiner* — J. Gregory Pickett
*Assistant Examiner* — Raven Collins
(74) *Attorney, Agent, or Firm* — Cook Alex Ltd.

(57) ABSTRACT

Containers and components thereof for use in the medical industry and methods to manufacture the same are described. An example tab for use with a medical container includes opposing sheets sealed to define an open ended chamber into which a port is to be at least partially positioned. The port is to enable access to the medical container. The tab includes a tear seal defined by each of the opposing sheets and a first guide positioned on a first side of each of the tear seals. The tab includes a second guide positioned on a second side of each of the tear seals, wherein the first and second guides are to enable a tear to propagate substantially between the guides and adjacent the tear seals.

23 Claims, 37 Drawing Sheets

2200

| | 2202 | 2204 | 2206 | 2208 | 2210 | 2212 | 2214 | 2216 |
|---|---|---|---|---|---|---|---|---|
| | | 4 psi | 6 psi | 8 psi | 12.5 psi | 16 psi | 20 psi | 25 psi |
| Polypropylene Homopolymer | 1 | OK | OK | OK | OK | OK | OK | Leaks |
| | 2 | OK | OK | OK | OK | OK | OK | Leaks |
| | 3 | OK | OK | OK | OK | OK | OK | OK |
| | 4 | OK | OK | OK | OK | OK | OK | Leaks |
| | 5 | OK | OK | OK | OK | OK | OK | OK |
| | | | | | | | | |
| Polypropylene Copolymer | 1 | OK | OK | OK | OK | OK | OK | OK |
| | 2 | OK | OK | OK | OK | OK | OK | OK |
| | 3 | OK | OK | OK | OK | OK | OK | OK |
| | 4 | OK | OK | OK | OK | OK | OK | Leaks |
| | 5 | OK | OK | OK | OK | OK | OK | OK |
| | | | | | | | | |
| Treated Polypropylene Homopolymer | 1 | OK | OK | OK | OK | OK | OK | Leaks |
| | 2 | OK | OK | OK | OK | OK | OK | Leaks |
| | 3 | OK | OK | OK | OK | OK | OK | OK |
| | 4 | OK | OK | OK | OK | OK | OK | Leaks |
| | 5 | OK | OK | OK | OK | OK | OK | OK |
| | | | | | | | | |
| Treated Polypropylene Copolymer | 1 | OK | OK | OK | OK | OK | OK | Leaks |
| | 2 | OK | OK | OK | OK | OK | OK | OK |
| | 3 | OK | OK | OK | OK | OK | OK | OK |
| | 4 | OK | OK | OK | OK | OK | OK | OK |
| | 5 | OK | OK | OK | OK | OK | OK | Leaks |

FIG. 22

CONTAINERS AND COMPONENTS THEREOF FOR USE IN THE MEDICAL INDUSTRY AND METHODS TO MANUFACTURE THE SAME

RELATED APPLICATIONS

This patent claims priority to U.S. Provisional Application No.: 61/180,544 filed May 22, 2009, U.S. Provisional Application No.: 61/229,998 filed Jul. 30, 2009, and U.S. Provisional Application No.: 61/240,022 filed Sep. 4, 2009, each of which is hereby incorporated herein by reference in its entirety.

FIELD OF THE DISCLOSURE

The present patent relates generally to containers and components thereof and, more particularly, to containers and components thereof for use in the medical industry and methods to manufacture the same.

BACKGROUND

Some containers may be used in the medical industry to store medical solutions, blood pack units or in other transfer pack applications. These containers may include ports to enable a substance(s) to be added to the contents contained within the container and/or to enable the contents to flow into or out of the container. To suspend the container from, for example, a hook, an end of the container may define a centrally located aperture.

BRIEF DESCRIPTION OF THE DRAWINGS

FIG. 22 depicts results obtained using the examples described herein.

DETAILED DESCRIPTION

Figure 1:
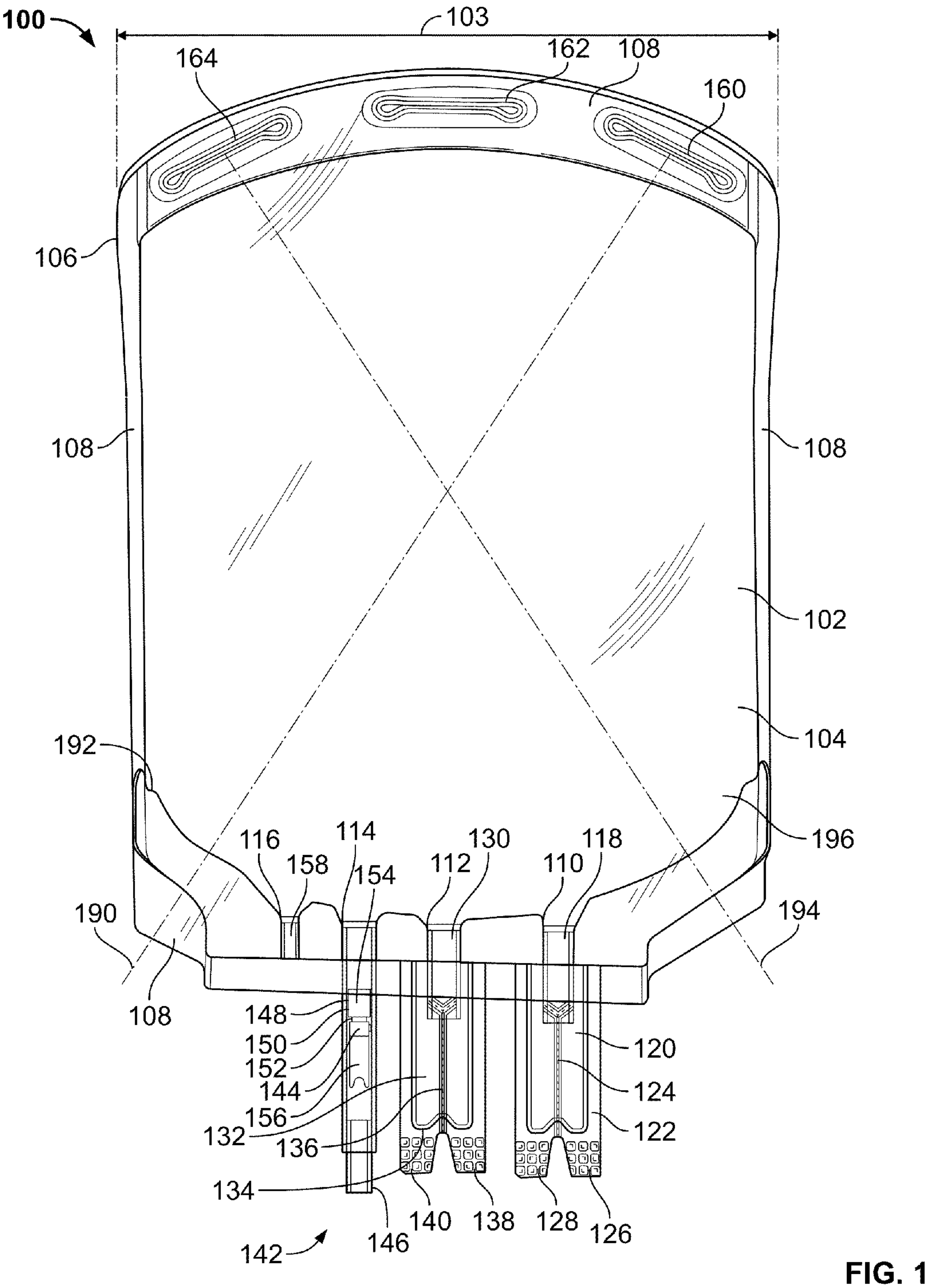
FIG. 1 depicts an example container.

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

The examples described herein relate to containers that may be used as medical solution or storage containers, blood pack units or in other transfer pack applications, for example. In some examples, the example containers described herein define a plurality of openings from which a membrane port or a frangible assembly may extend and a plurality of apertures from which the container may be suspended. Providing the example containers described herein with the plurality of apertures, enables the containers described herein to be suspended at different angles relative to the floor, thereby decreasing the likelihood that particulate or clots will disrupt and/or affect fluid flow to and from the container.

The frangible assemblies described herein may include a frangible housing, a frangible positioned in the frangible housing and a bushing to be engaged by a portion of the frangible once separated. In some examples, the frangible housing may have a substantially consistent inner diameter to enable a length of the frangible housing and/or an area provided within the frangible housing to be relatively easily tailored to a particular application.

To maintain the sterility of the membrane ports, a tab having a tear seal may encase a portion of the membrane port that extends from the container. To access the membrane port positioned in the example tabs described herein, a person may grasp the first grip tab with one hand and the second grip tab with the other hand and then move the tabs in opposite directions, thereby initiating a tear proximate the tear initiation area. Once the tear has been initiated, the person may continue to move the tabs in opposite directions to propagate the tear along, for example, the tear seal and/or between guides positioned on either side of the tear seal. Such an approach enables relatively easy access to the membrane port with a reduced opening force and provides a relatively reliable tear seal as compared to the prior art. Additionally, such tabs may be functional over a broad temperature range such as, for example, between about one degree Celsius and forty degrees Celsius. While the examples described herein describe example tabs including the example tear seals, the example tear seals described herein may be advantageously formed on other structures. For example, the tear seals may be formed on a container bag panel, etc. The example tabs including tear seals may be used with containers in the medical industry such as, for example, medical solution or storage containers, blood pack units or other transfer pack applications. In some examples, the tabs include sheets of material coupled together along some edges to form an open ended chamber into which, for example, a membrane port may be positioned. Additionally, the tabs described herein may include a first grip tab and a second grip tab between which a tear initiation area or point may be positioned. In some examples, the example tabs described herein may be coupled between sheets of a medical container. Alternatively, in some examples, the example tabs described herein may be an integral extension of and/or integrally coupled to the respective sheets of the medical container.

The examples described herein relate to methods and apparatus to enable typically non-solvent bondable materials (e.g., polypropylene, a low molecular weight polypropylene, a high melt flow polypropylene, polyethylene, polymethylpentene) to be solvent bonded to, for example, polyvinyl chloride. As used herein solvent bonding refers to solvent sealed bonding of two dissimilar materials by solvation of one or more materials, thereby enabling the formation of an adhesive bond between the two dissimilar materials. Such an approach of enabling non-solvent bondable materials to be solvent bondable enables ports used with medical apparatus to be made of a material(s) that is substantially less expensive as well as less dense as compared to materials that are currently being used such as, for example, polycarbonate. Additionally, enabling ports or other apparatus to be made of, for example, polypropylene, enables the examples described herein to be relatively more resistant to environmental stress cracking while still being able to be sterilized by different methods such as, for example, radiation sterilization, steam sterilization, ethylene oxide sterilization, etc. Further, enabling ports or other apparatus to be made of, for example, polypropylene, enables non-treated or uncoated portions of the examples described herein to substantially not bond (e.g., thermally bond) to, for example, polyvinyl chloride, during autoclaving.

FIG. 1 depicts an example container 100 having a compartment 102 for storage of a substance(s) and/or solution(s). In some examples, the container 100 may be used as a medical solution or storage container, a blood pack unit or for some other transfer pack application. A width 103 of the container 100 may be relatively wide as compared to some known containers (not shown). Increasing the width 103 of the container 100 may enable the container 100 to be more fully supported within a centrifugation cup (not shown) in which the container 100 may be positioned. The container 100 may be formed using a first sheet 104 and a second sheet 106 opposite the first sheet 104. The sheets 104 and 106 may be relatively flexible and may be made of any suitable material such as, for example, a Polyvinyl chloride material, a non-Polyvinyl chloride, an olefin material, a poly-olefin material and/or a bis(2-ethylhexyl)phthalate material free material. To contain and prevent the leakage of the substance(s) and/or solution(s) stored within the compartment 102, the sheets 104 and 106 may be sealed (e.g., heat sealed, adhesive bonding, etc.) along a peripheral edge 108 to form a substantially permanent seal between the sheets 104 and 106. The compartment 102 may be any suitable size depending on the particular application and, in some instances, may be between about 150 ml and 2000 ml.

Figure 2:
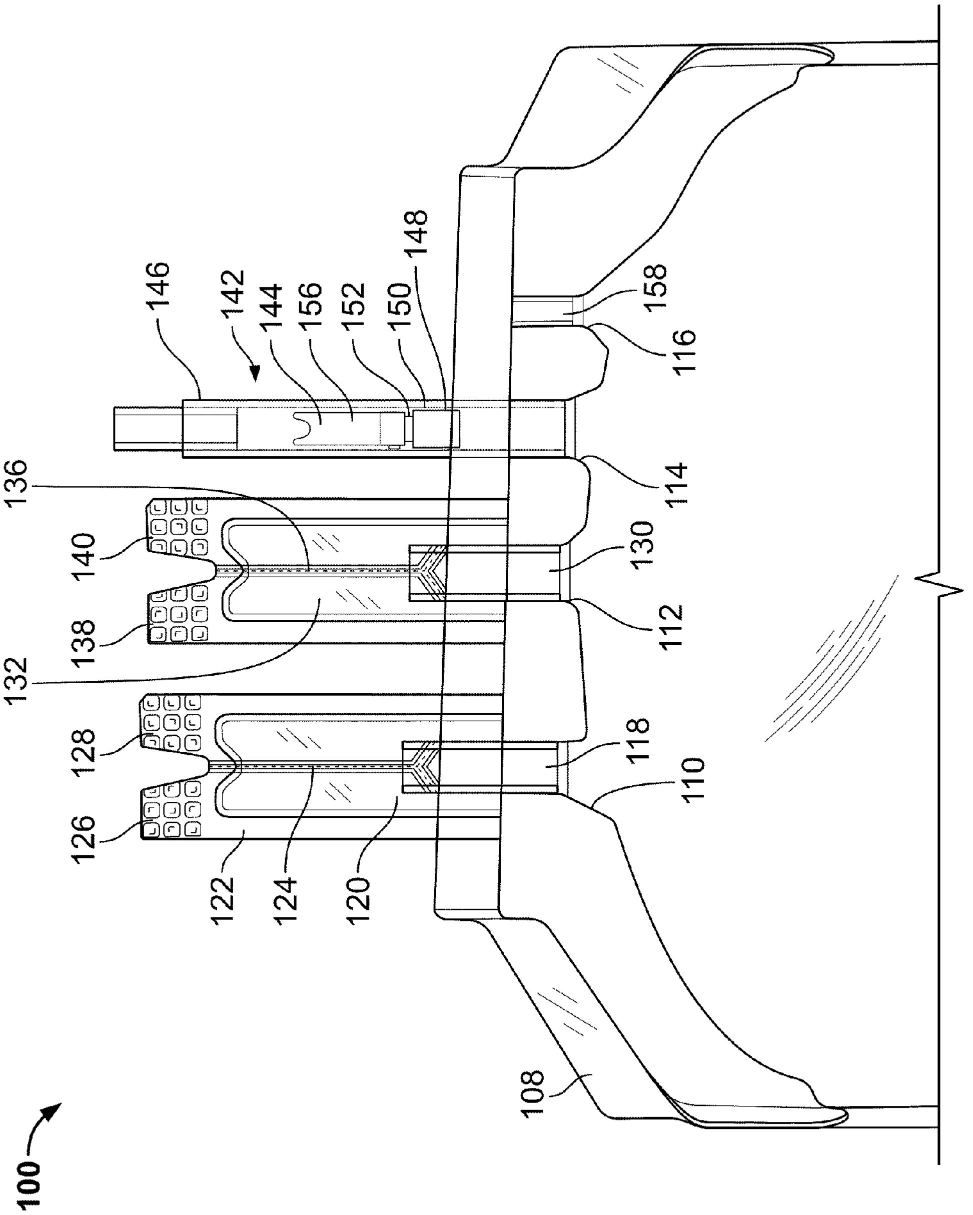
FIG. 2 depicts a portion of the example container of FIG. 1.

To enable access to the compartment 102, as shown most clearly in FIG. 2, the container 100 is provided with a first opening or aperture 110, a second opening or aperture 112, a third opening or aperture 114 and a fourth opening or aperture 116; however, any number of apertures (e.g., 1, 2, 3, 4, 5, etc.) may be provided instead. In this example, a first membrane port or tube 118 is positioned within the first opening 110 and, to maintain the sterility of the first membrane port 118 during handling, a portion of the first membrane port 118 extending from the peripheral edge 108 is positioned in a chamber 120 defined by an example first tab 122. In some examples, the first tab 122 may be positioned between the sheets 104 and 106. Alternatively, in some examples, the first tab 122 may be formed from and/or an integral extension of the sheets 104 and 106. When a person wants to access the first membrane port 118, the first tab 122 may be torn along a tear seal 124 by moving grip tabs 126 and 128 in opposite directions, thereby propagating the tear along the tear seal 124.

Similarly, a second membrane port or tube 130 is positioned within the second opening 112 and, to maintain the sterility of the second membrane port 130 during handling, a portion of the second membrane port 130 extending from the peripheral edge 108 is positioned within a chamber 132 of an example second tab 134. When a person wants to access the second membrane port 130, the second tab 134 may be torn along a tear seal 136 by moving grip tabs 138 and 140 in opposite directions, thereby propagating the tear along the tear seal 136.

To prevent fluid flow through the third opening 114, a frangible assembly 142 is partially positioned in and extends from the third opening 114. The frangible assembly 142 includes a frangible 144 positioned within a frangible housing 146 and has an outer surface 148 that is coupled to an inner surface 150 of the frangible housing 146 to prevent fluid flow between the surfaces 148 and 150. The frangible 144 may be broken along a frangible joint 152 to separate a port 154 of the frangible 144 from an elongated member 156 of the frangible 144. Once the frangible 144 is separated, the elongated member 156 may move away from the port 154, thereby enabling fluid flow through the frangible assembly 142. The fourth opening 116 is provided with a third membrane tube or port 158 and, in this example, is not provided with one of the example tabs; however, a tab similar to the first tab 122 or the second tab 134 may be provided.

Figure 3:
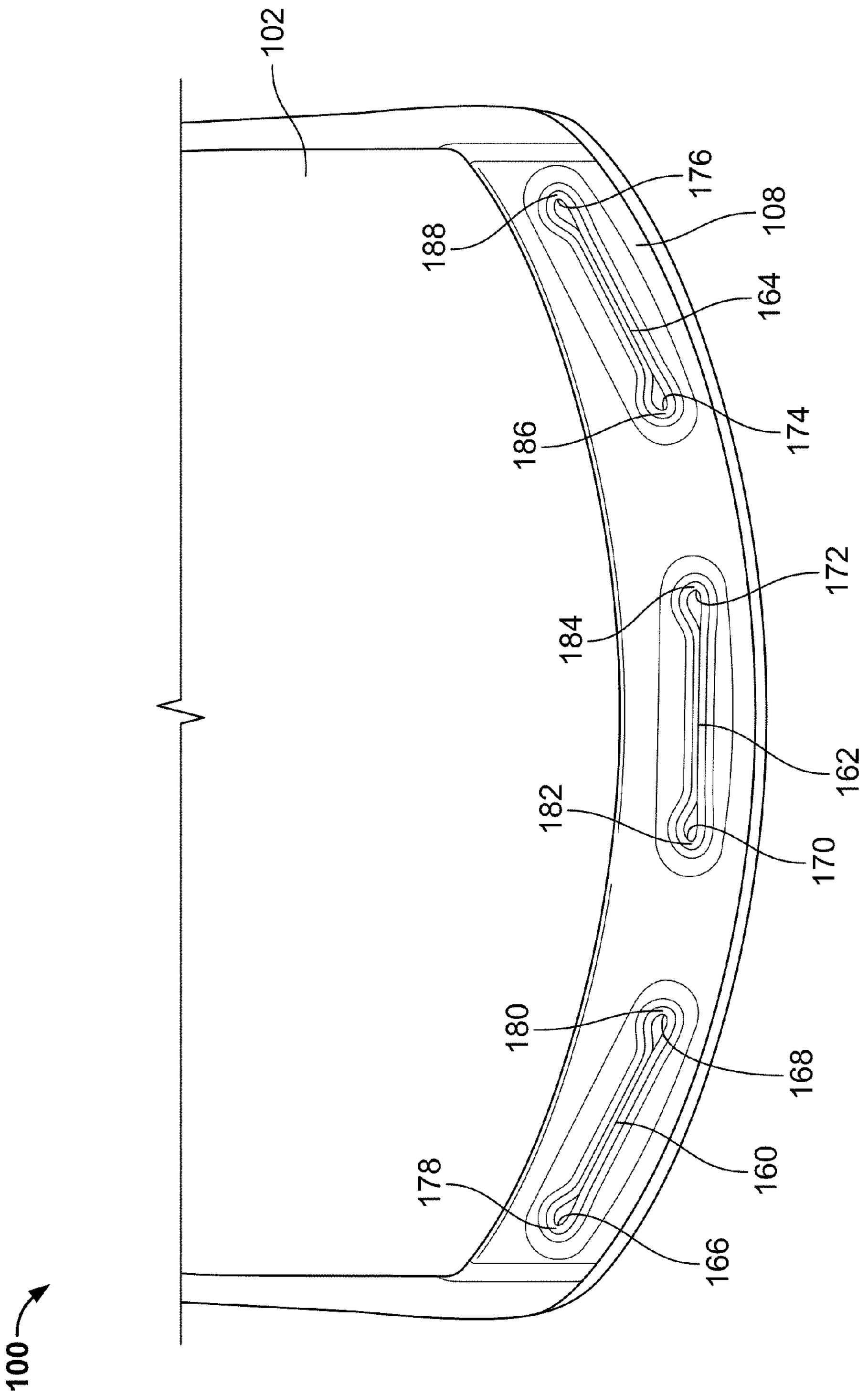
FIG. 3 depicts another portion of the example container of FIG. 1.

Opposite the openings 110-116, and most clearly shown in FIG. 3, the peripheral edge 108 defines a first aperture 160, a second aperture 162 and a third aperture 164 each of which may be utilized to suspend or hang the container 100 at different angles relative to a floor (not shown) and/or to store a tube segment(s) or a donor sample tube(s), for example. The apertures 160-164 may be generally positioned in the middle of the peripheral edge 108 to decrease the likelihood that an unwanted tear will develop adjacent the aperture 160-164 from which the container 100 is suspended. If a tear would develop adjacent the aperture 160-164 from which the container 100 is suspended, the tear may result in the container 100 falling to the floor, for example.

Additionally or alternatively, to further decrease the likelihood that an unwanted tear will develop adjacent the apertures 160-164 from which the container 100 is suspended, each of the apertures 160-164 includes radii or curved portions 166-176. These curved portions 166-176 substantially decrease stress points on ends 178-188 of the apertures 160-164 adjacent the curved portions 166-176, which may otherwise be caused by the weight of the container 100 and any other apparatus (not shown) supported by the container 100. The apertures 160-164 may be similarly or differently sized and may, in some examples, have a length of between about ¼ inch to 1.0 inch.

In practice, if the container 100 is suspended from the first aperture 160, an axis 190 of the container 100 may be substantially perpendicular to the floor. Thus, if particulate and/or solids form within the substance(s) and/or solution(s) contained within the compartment 102, the particulate(s) and/or solid(s) may accumulate toward a corner 192 of the compartment 102 instead of flowing toward and impacting and/or obstructing fluid flow through one of the openings 110-116. If the substance or solution is blood, these particulate and/or solids may form in the blood if anti-coagulant is added to the blood and is not sufficiently mixed. Similarly, if the container 100 is suspended from the third aperture 164, an axis 194 of the container 100 may be substantially perpendicular to the floor, thereby enabling the particulate(s) and/or solid(s) to accumulate toward a corner 196 of the compartment 102.

Figure 4:
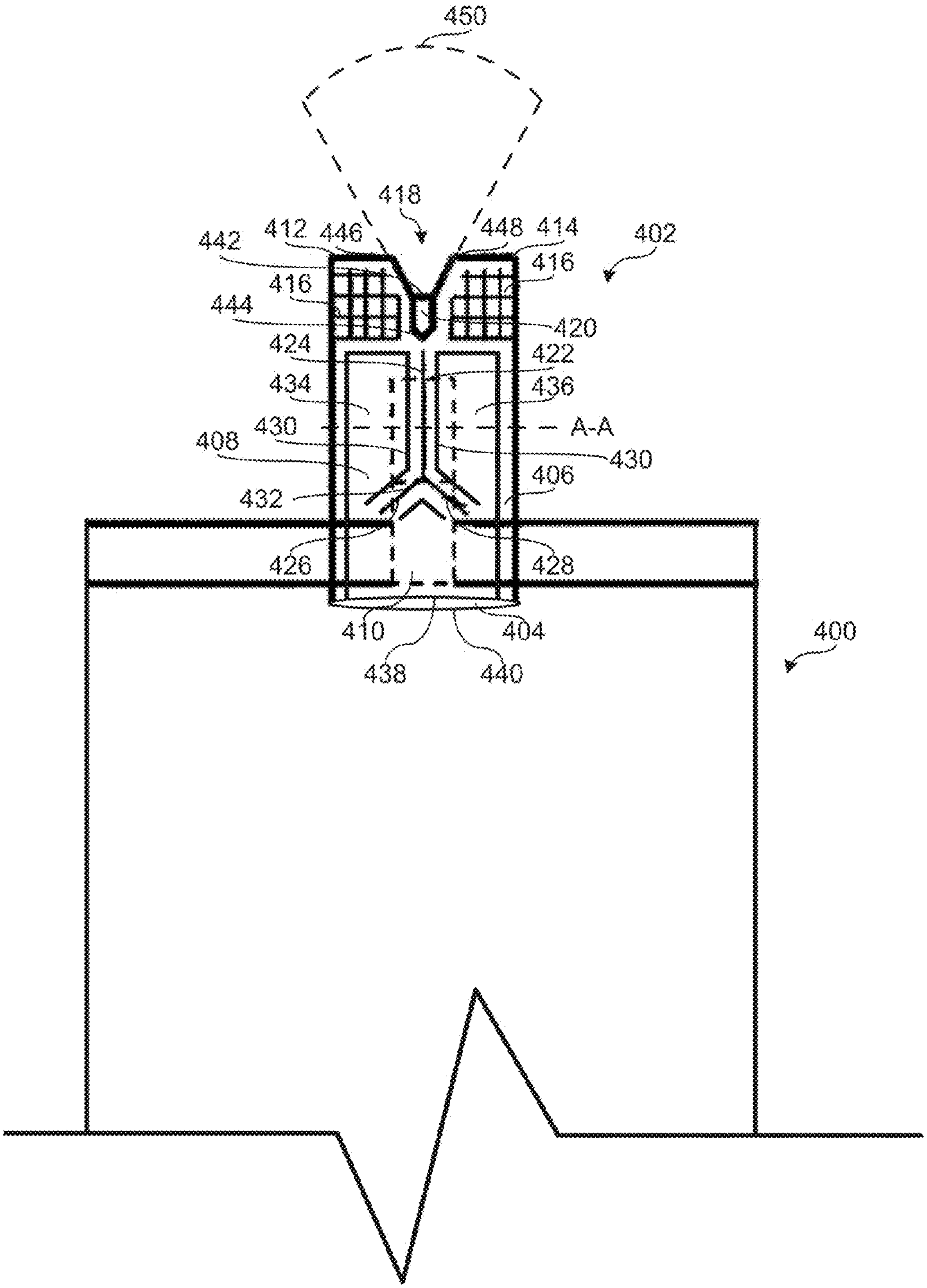
FIG. 4 depicts another container and an example tab.

FIG. 4 depicts a container 400 coupled to an example tab 402 via, for example, radio frequency (RF) sealing or any other suitable method. The container 400 and/or the example tab 402 may be used to implement at least a portion of any of the examples described herein. The example tab 402 may include an opening 404 positioned within the container 400 and a perimeter seal 406 (e.g., a hermetic seal) that surrounds a chamber 408 of the tab 402 into which a membrane port or tube 410 is positioned. Generally, the perimeter seal 406 prevents contaminants from coming into contact with the membrane port 410. Additionally, the example tab 402 includes a first grip tab 412 opposite a second grip tab 414 that each include a plurality of projections 416 produced via, for example, an RF sealing process. The plurality of projections 416 may further enable a person to grip the respective first and/or second grip tabs 412 and/or 414. Additionally, the location of the projections 416 and/or the grip tabs 412 and 414 relative to the example tab 402 may indicate to a person the proper and/or intended usage of the tab 402.

A notch 418 is positioned between the grip tabs 412 and 414 to focus a force (e.g., a shear force), applied by a person, as discussed below, to a tear initiation area or point 420. The notch 418 is positioned adjacent to the tear initiation area 420. Additionally, the example tab 402 may include a tear seal 422 (e.g., a hermetic seal) having a lateral portion 424 and first and second tapered portions 426 and 428 positioned between a plurality of guides, reinforcing features, ribs or extrusions 430. The lateral portion 424 may have a first end proximate the tear initiation area 420 and a second end proximate the first and second tapered portions 426 and 428. In some examples, one or more of the plurality of guides 430 may have a height of approximately 0.016 inches, which may prevent the tear from wondering from between the plurality of guides 430 as the tab 402 is separated, as discussed below.

In operation, a person may grasp the first grip tab 412 with one hand and the second grip tab 414 with the other hand and then apply a first force in a first direction to the first grip tab 412 and a second force in a second direction, opposite the first direction, to the second grip tab 414, such that a shear movement initiates a tear (not shown) adjacent or proximate the tear initiation area 420. Once the tear is initiated, the person may continue to apply the first force in the first direction to the first grip tab 412 and the second force in the second direction to the second grip tab 414, thereby propagating the tear along, for example, the lateral portion 424 of the tear seal 422 and/or between the guides 430 and toward the first and second tapered portions 426 and 428. As the tear reaches a junction 432 between the portions 424, 426 and/or 428, the tear may split such that a tear follows the first tapered portion 426 and another tear follows the second tapered portion 428 or the tear follows one of the first tapered portion 426 or the second tapered portion 428. Enabling the tear to follow the first tapered portion 426 and/or the second tapered portion 428 further separates a first portion 434 and a second portion 436 of the example tab 402, thereby enabling the membrane port 410 to be more easily accessed and/or substantially prevents the portions 434 and 436 from again coming together once separated. Additionally or alternatively, the ease of use may be enhanced because the first and second portions 434 and 436 remain attached to the tab 402 and, thus, a separated component is not created to be handled while or prior to attempting to access the membrane port 410.

The example tab 402 may be fabricated, manufactured and/or produced from a first sheet or film 438 of material and a second sheet or film 440 of material that are each to have at least one opposing tear seal 422. The first and second sheets 438 and 440 may be joined together via any suitable method such as, for example, RF sealing, along the perimeter seal 406. The first sheet 438 and/or the second sheet 440 may be made of any suitable material such as, for example, a plastic material, a bis(2-ethylhexyl)phthalate (DEHP) free material, a polyolefin material or a polyvinyl chloride (PVC) material that may have a thickness of between about 0.006 inches and 0.02 inches. Specifically, in some examples, the first and/or second sheets 438 and/or 440 may be a PL-146 PVC material that has a thickness of approximately 0.0145 inches.

Similarly, the first grip tab 412 and the second grip tab 414 may be made of any suitable material that is similar or different from the material of the first and second sheets 438 and/or 440 such as, for example, a plastic material or a Polyvinyl chloride (PVC) material. In some examples, the first and/or second grip tabs 412 and/or 414 may have a thickness of between about 0.006 inches and 0.02 inches or approximately 0.0135 inches, a durometer range of between about sixty shore A and ninety shore A and a shear modulus range of between about two hundred pounds per square inch (PSI) and twenty thousand PSI. However, preferably, in some examples, the shear modulus range of the first and/or second grip tabs 412 and/or 414 may be between about six hundred PSI and one thousand PSI.

The tear initiation area or point 420 may be made of any suitable material such as, for example, a PVC material, and may be fabricated via an RF sealing process. The tear initiation area 420 may a thickness of between about 0.002 inches and 0.015 inches. However, preferably, in some examples, the thickness of the tear initiation area 420 may be approximately 0.007 inches. Generally, the thickness of the tear initiation area 420 may be between about zero percent and seventy percent of the material thickness of the first and/or second sheets 438 and/or 440 and/or the total material thickness. However, preferably, in some examples, the thickness of the tear initiation area 420 may be approximately thirty percent of the material thickness of the first and/or second sheets 438 and/or 440 and/or the total material thickness. In some examples, the thickness of the tear initiation area 420 may vary between an edge 442 and a trailing edge 444 of the tear initiation area 420.

First and second edges 446 and 448 of the first and second grip tabs 412 and 414 may define the notch 418 having an angle 450 of between about fifteen degrees and one hundred and twenty degrees. However, preferably, in some examples, the angle 450 between the first and second edges 446 and 448 may be between about thirty degrees and ninety degrees. Generally, the angle 450 focuses a force applied by a person toward the tear initiation area 420 when the person moves the grip tabs 412 and 414 in opposite directions to separate the portions 434 and 436 to gain access to the membrane port 410.

The tear seal 422 may be made of any suitable material such as, for example, a PVC material, having a thickness of between about 0.002 inches and 0.015 inches or between about 0.0045 inches and 0.011 inches. However, preferably, in some examples, the thickness of the tear seal 422 may be approximately 0.005 inches. Generally, the thickness of the tear seal 422 may be between about ten percent and seventy percent of the material thickness of the first and/or second sheets 438 and/or 440 and/or the total material thickness. However, preferably, in some examples, the thickness of the tear seal 422 may be approximately thirty percent of the material thickness of the first and/or second sheets 438 and/or 440 and/or the total material thickness. In some examples, a width of the tear seal 422 may be approximately 0.007 inches. While the tab 402 includes one tear seal 422 on the first sheet 438 and one tear seal 422 on the second sheet 440, any number of tear seals (e.g., 1, 2, 3, etc.) may be fabricated on the first sheet 438 and/or the second sheet 440 to facilitate manufacturability and/or to enable alignment with the tear initiation area 420 irrespective of manufacturing tolerances.

Figure 5:
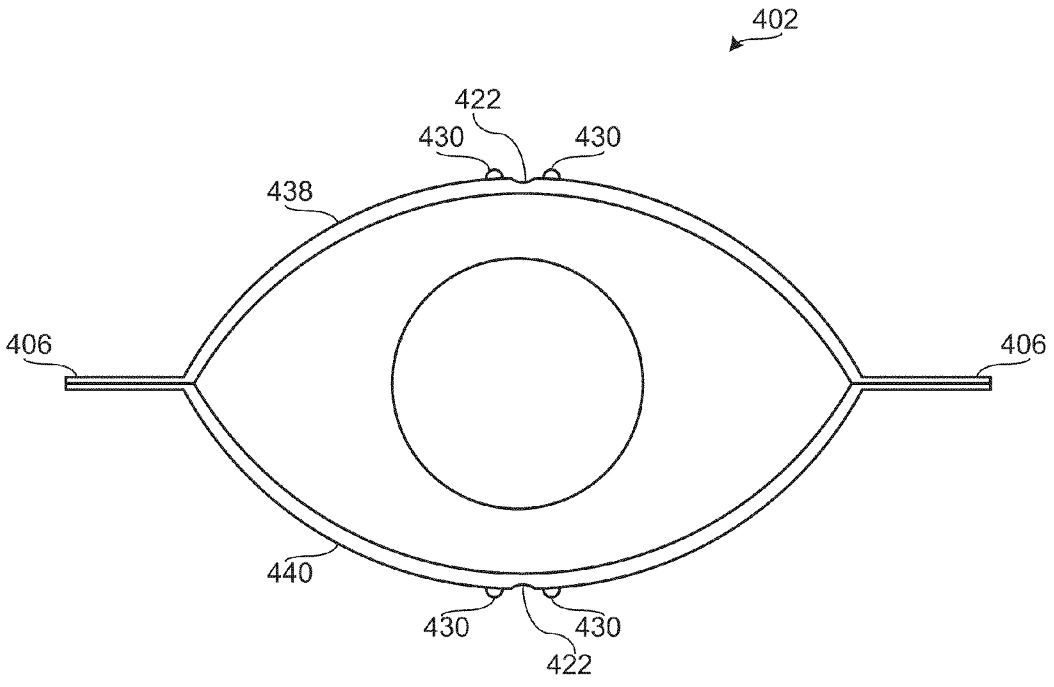
FIG. 5 depicts a cross-sectional view along line A-A of FIG. 4.

FIG. 5 depicts the sheets 438 and 440 including the example guides 430 and tear seals 422 along A-A of FIG. 4. Additionally, FIG. 5 depicts the membrane port 410 positioned in the chamber 408 defined by the sheets 438 and 440.

Figure 6:
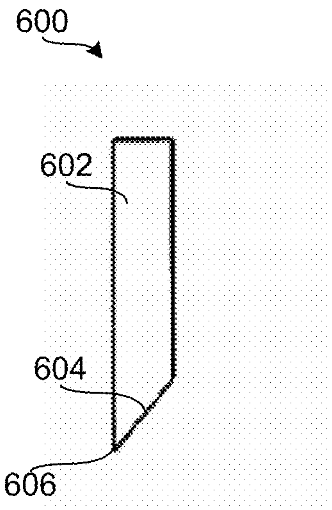
FIG. 6 depicts an example die that may be utilized to fabricate an example tear seal.

FIG. 6 depicts a portion of an example die 600 that may be used during a fabricating process to produce, for example, the tear seal 422 (FIG. 4) of the example tab 402 (FIG. 4). The die 600 includes a body 602 that may have a thickness of approximately 0.187 inches and a tapered surface 604 having an angle of approximately forty five degrees. In operation, in some examples, a two kilowatt (KW) RF generator (not shown) may be utilized along with the example die 600 to form the tear seal 422. Specifically, the RF generator may be adjusted to approximately thirty percent power and the die 600 may be moved toward a sheet (e.g., the first sheet 438 or the second sheet 440) with a press air pressure of approximately 80 PSI until an end or tip 606 of the die 600 engages the sheet and a die gap exists of approximately 0.005 inches. RF energy is then applied via the die 600 to the sheet for a seal time of approximately three seconds along with the compression force (e.g., approximately 80 PSI) applied by the die 600. After the RF-energy has been applied to the sheet, the die 600 may remain adjacent the sheet for a hold time of approximately five seconds, thereby producing the tear seal 422 on the sheet. Such an approach increases the reliability and/or consistency of the tear seal 422 and/or decreases the control requirements to produce tear seals 422 having substantially consistent opening characteristics, which eliminates the limitations encountered by the prior art.

Figure 7:
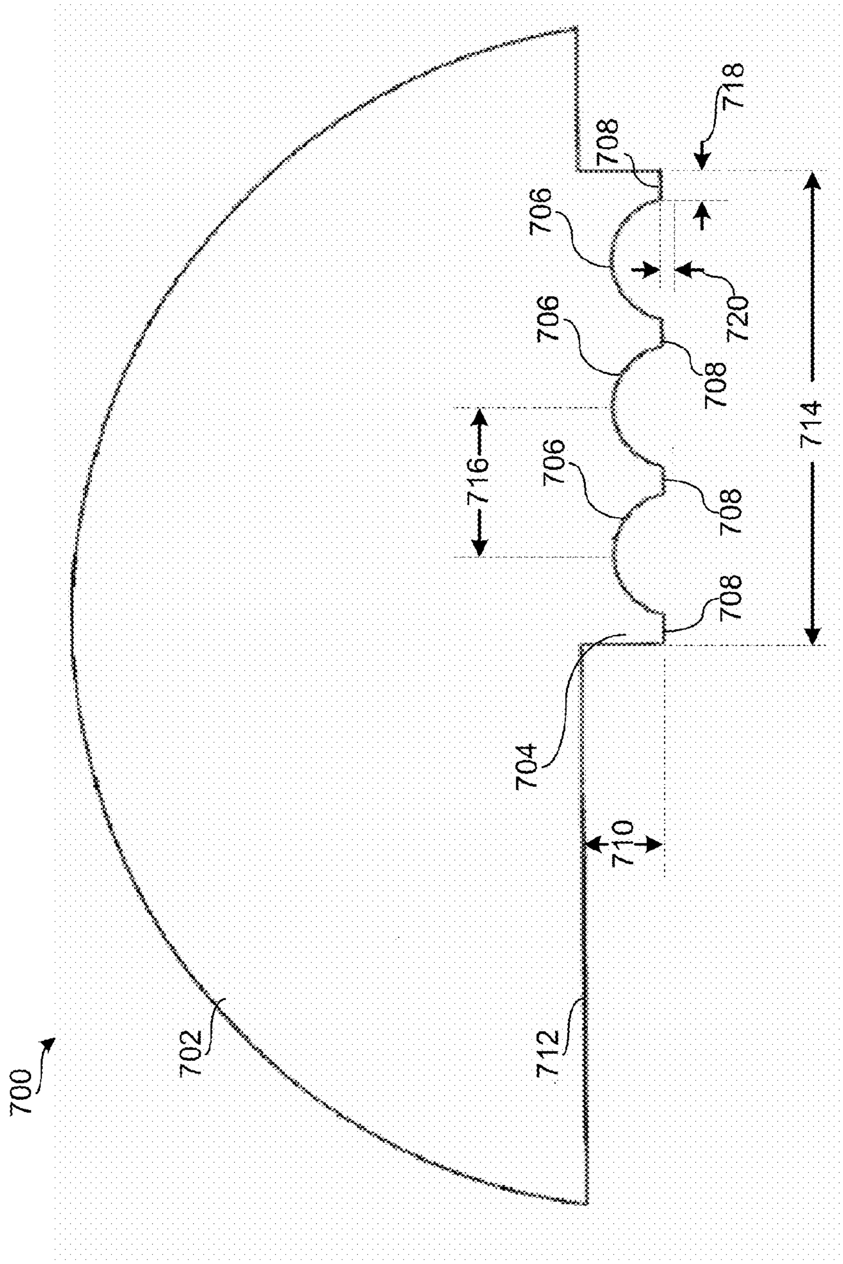
FIG. 7 depicts a portion of another example die that may be utilized to fabricate an example tear seal.
Figure 8:
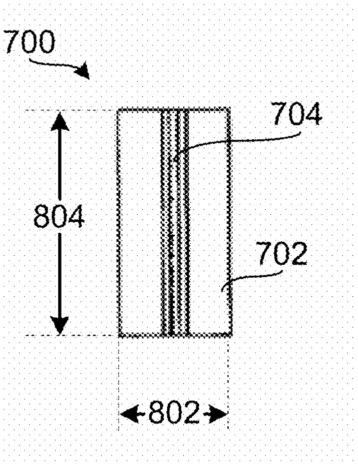
FIG. 8 depicts a top view of the example die of FIG. 7.
Figure 9:
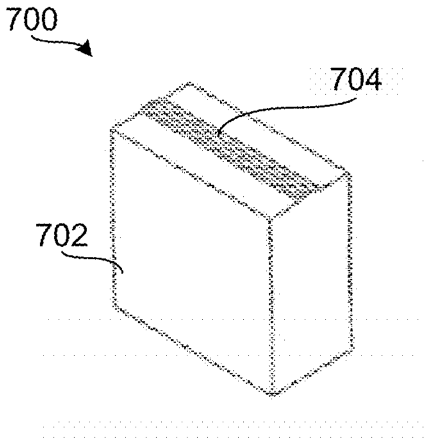
FIG. 9 depicts an alternative view of the example die of FIG. 7.
Figure 10:
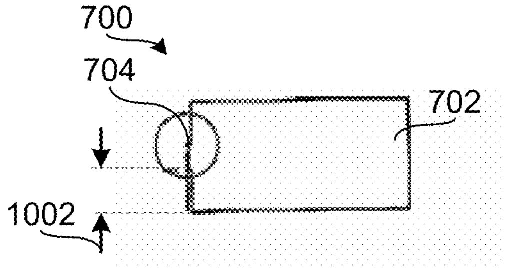
FIG. 10 depicts a side view of the example die of FIG. 7.
Figure 11:
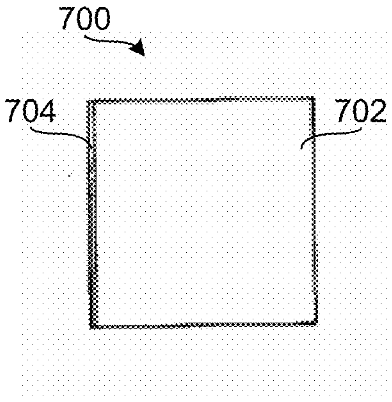
FIG. 11 depicts an alternative side view of the example die of FIG. 7.
Figure 12:
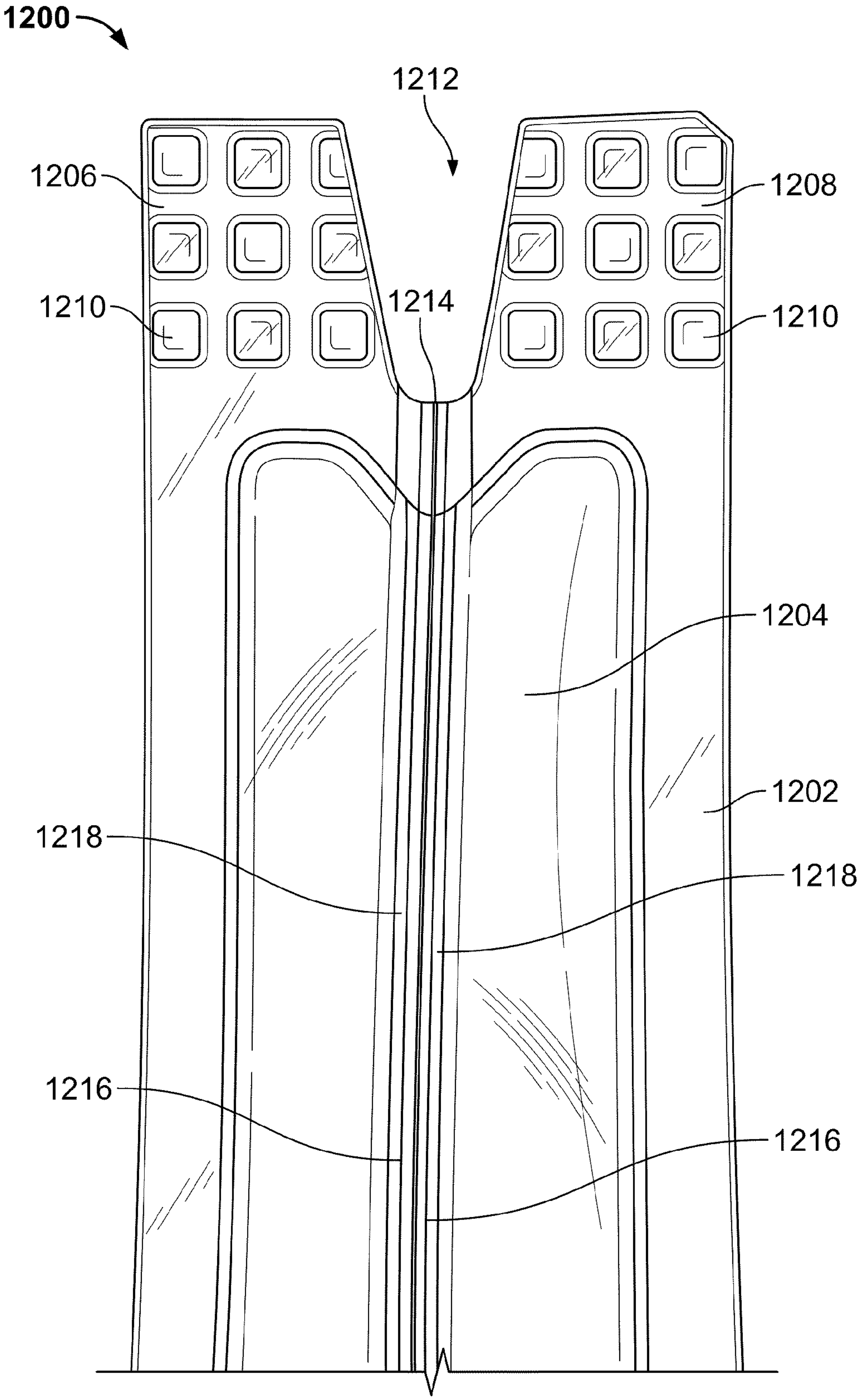
FIGS. 12-15 depict various views of another example tab.

FIG. 7 depicts a portion of another example die 700 that may be used during a fabricating process to produce, for example, the tear seal 422 (FIG. 4) and/or the plurality of guides 430 (FIG. 4) of the example tab 402 (FIG. 4). The example die 700 includes a body 702 having an offset portion 704 that defines a plurality of spaced grooves 706 that, in this example, have a semi-annular shape. In some examples, the plurality of spaced grooves 706 may have a radius of approximately 0.015 inches. In operation, in some examples, an RF generator (not shown) may be utilized along with the example die 700 to form the tear seal 422 and/or the plurality of guides 430. Specifically, the die 700 may be moved toward a sheet (e.g., the first sheet 438 or the second sheet 440) with a predetermined press air pressure until at least one of a plurality of surfaces 708 adjacent and/or between the plurality of grooves 706 engages the sheet. RF energy is then applied via the die 700 to the sheet for a predetermined seal time, which melts a portion of the sheet adjacent each of the surfaces 708, along with the compression force (e.g., the predetermined press air pressure) applied by the die 700. As the portion of the sheet melts, the melted portion flows toward and extrudes into one or more of the plurality of grooves 706, thereby forming the plurality of the guides 430 and the plurality of the tear seals 422 adjacent each of the surfaces 708. Generally, as the RF energy is applied to the sheet, a thickness of the sheet adjacent each of the surfaces 708 decreases respectively fabricating one of the tear seals 422 and a thickness of the sheet adjacent each of the plurality of grooves 706 increases respectively fabricating one of the guides 430. After the RF energy is applied to the sheet, the die 700 may remain adjacent the sheet for a predetermined hold time. While the example die 700 of FIG. 7 includes three grooves 706 and four surfaces 708, the example die 700 may include any number of grooves 706 (e.g., 1, 2, 3, etc.) and any number of surfaces 708 (e.g., 1, 2, 3, etc.) to produce and/or fabricate any number (e.g., 1, 2, 3, etc.) of corresponding tear seals 422 or guides 430. While the plurality of grooves 706 of the example die 700 of FIG. 7 each have a semi-annular shape, some or all of the grooves 706 may have any other suitable shape (e.g., a triangular shape, include a point). In some examples, a distance 710 between a surface 712 and the plurality of surfaces 708 may be approximately 0.020 inches. In some examples, a width 714 of the offset portion 704 may be approximately 0.115 inches. In some examples, a distance 716 between two of the plurality of grooves 706 may be approximately 0.036 inches. In some examples, a width 718 of one of the plurality of surfaces 708 may be approximately 0.007 inches. In some examples, a distance 720 between the plurality of surfaces 708 and an opposing die and/or a thickness of a tear seal formed on a sheet is approximately 0.003 inches. Alternatively, in some examples, the distance 720 is between about 0.003 inches and 0.007 inches, and preferably approximately 0.005 inches. FIGS. 8-11 depict various views of the example die 700. In some examples, a width 802 of the die 700 may be approximately 0.5 inches. In some examples, a length 804 of the die 700 may be approximately 1.0 inch. In some examples, a distance 1002 between the offset portion 704 and a surface of the die 700 may be approximately 0.192 inches.

FIGS. 12-15 depict various views of an example tab 1200 that is substantially similar to the example tab 402 discussed above in connection with FIG. 4 and may be used to implement at least a portion of any of the examples described herein. The example tab 1200 includes a perimeter seal 1202 that surrounds a chamber 1204 of the tab 1200 into which a membrane port or tube (not shown) is to be positioned. Additionally, the example tab 1200 includes a first grip tab 1206 opposite a second grip tab 1208 that each include a plurality of projections 1210.

A notch 1212 is positioned between the grip tabs 1206 and 1208 to focus a force (e.g., a shear force), applied by a person, to a tear initiation area or point 1214. Additionally, the example tab 1200 includes a plurality of tear seals 1216 adjacent a plurality of guides, reinforcing features or extrusions 1218. Including the plurality of tear seals 1216 on the example tab 1200 may substantially ensure that one of the plurality of tear seals 1216 is aligned with the tear initiation area 1214 and/or the tear initiated in the tear initiation area 1214, which enables the example tab 1200 to be opened even taking into account manufacturing tolerances of the tear seal 1216. Additionally, including the plurality of guides 1218 on the example tab 1200 may substantially ensure that the tear does not wonder from between the guides 1218 and/or follows one of the plurality of tear seals 1216 as the tear propagates. The example tab 1200 may be opened using a similar method as discussed above. As such, a description will not be repeated here. Additionally, the example tab 1200 may be produced and/or fabricated using a similar process as discussed above. As such, a description will not be repeated here.

Figure 13:
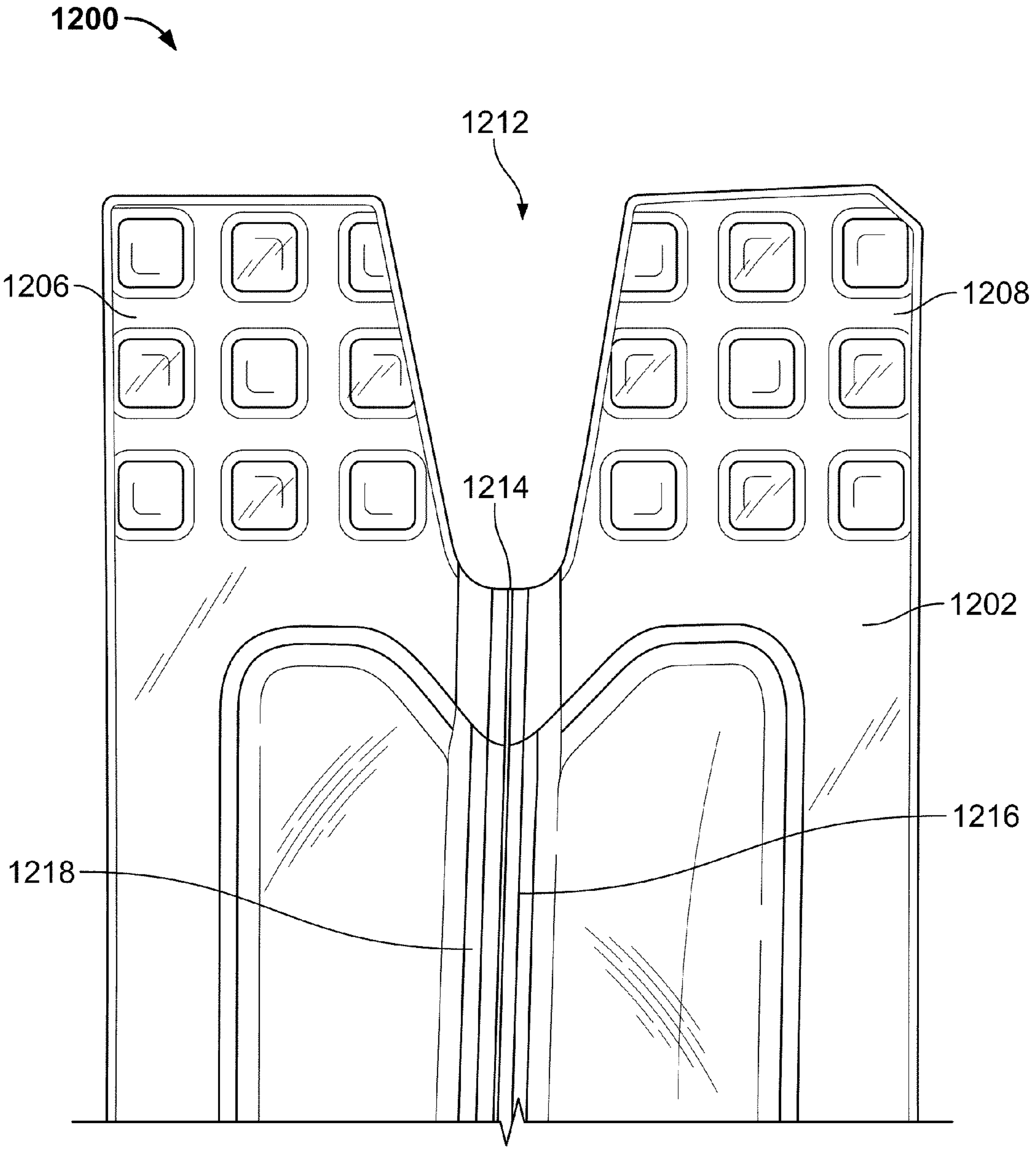
Figure 14:
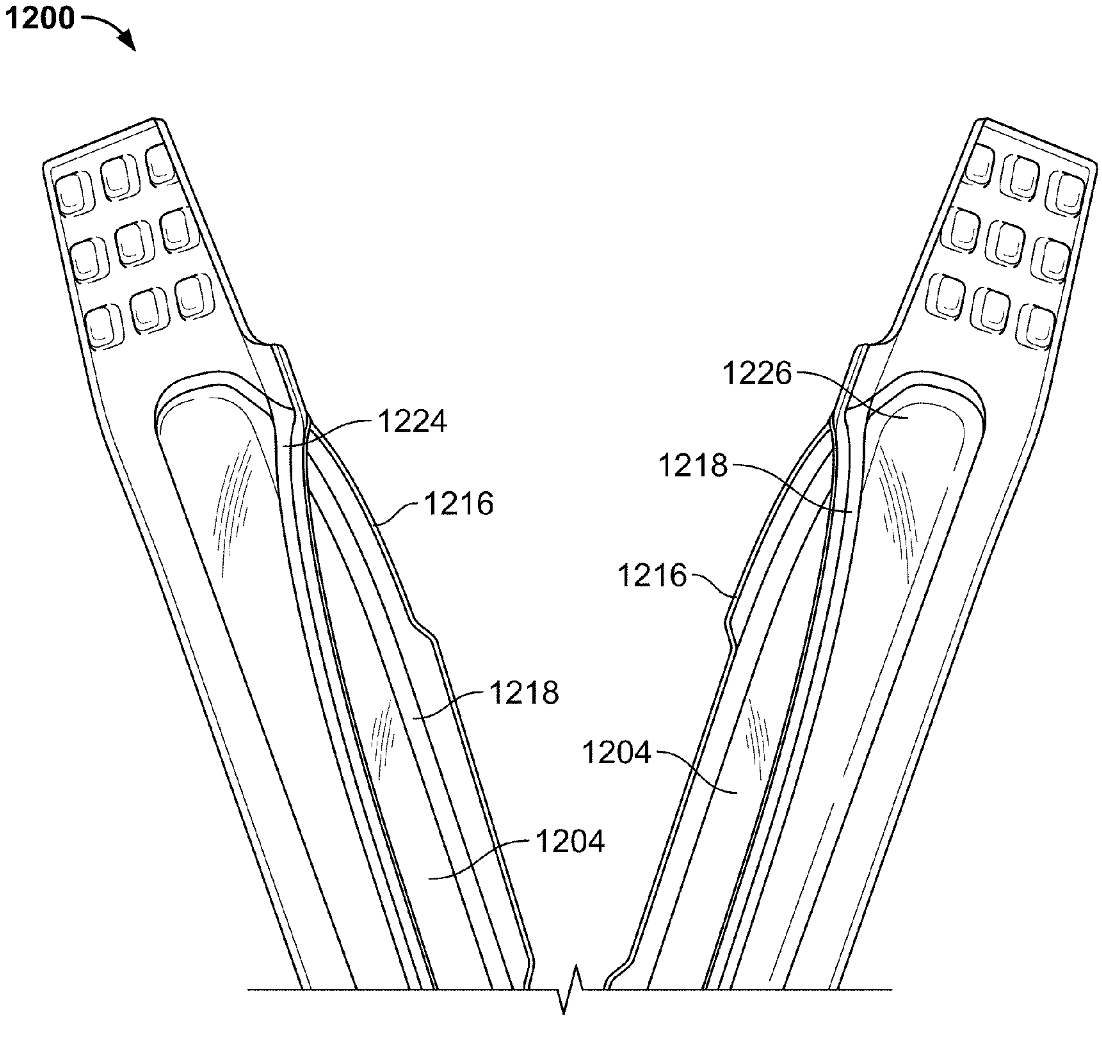
Figure 15:
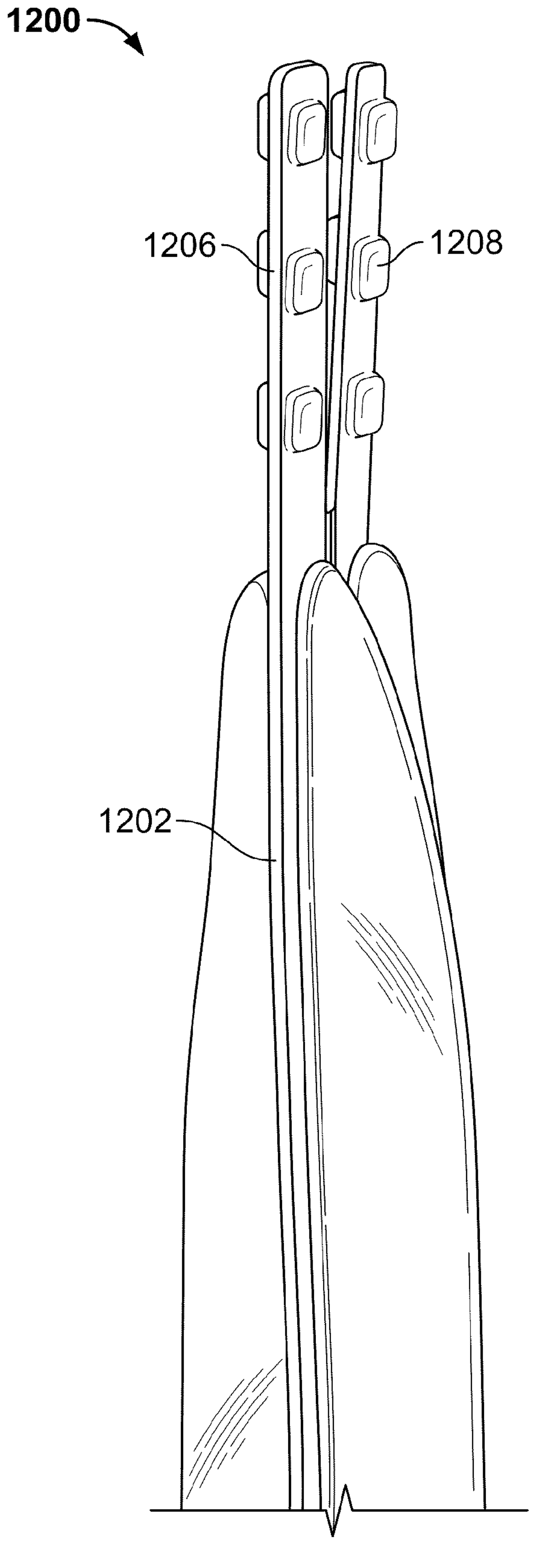

FIG. 13 depicts an enlarged view of the example tab 1200. FIG. 14 depicts the example tab 1200 separated or torn along the tear seal 1216 and/or between the guides 1218 into a first portion 1224 and a second portion 1226. FIG. 15 depicts a side view of the example tab 1200.

Figure 16:
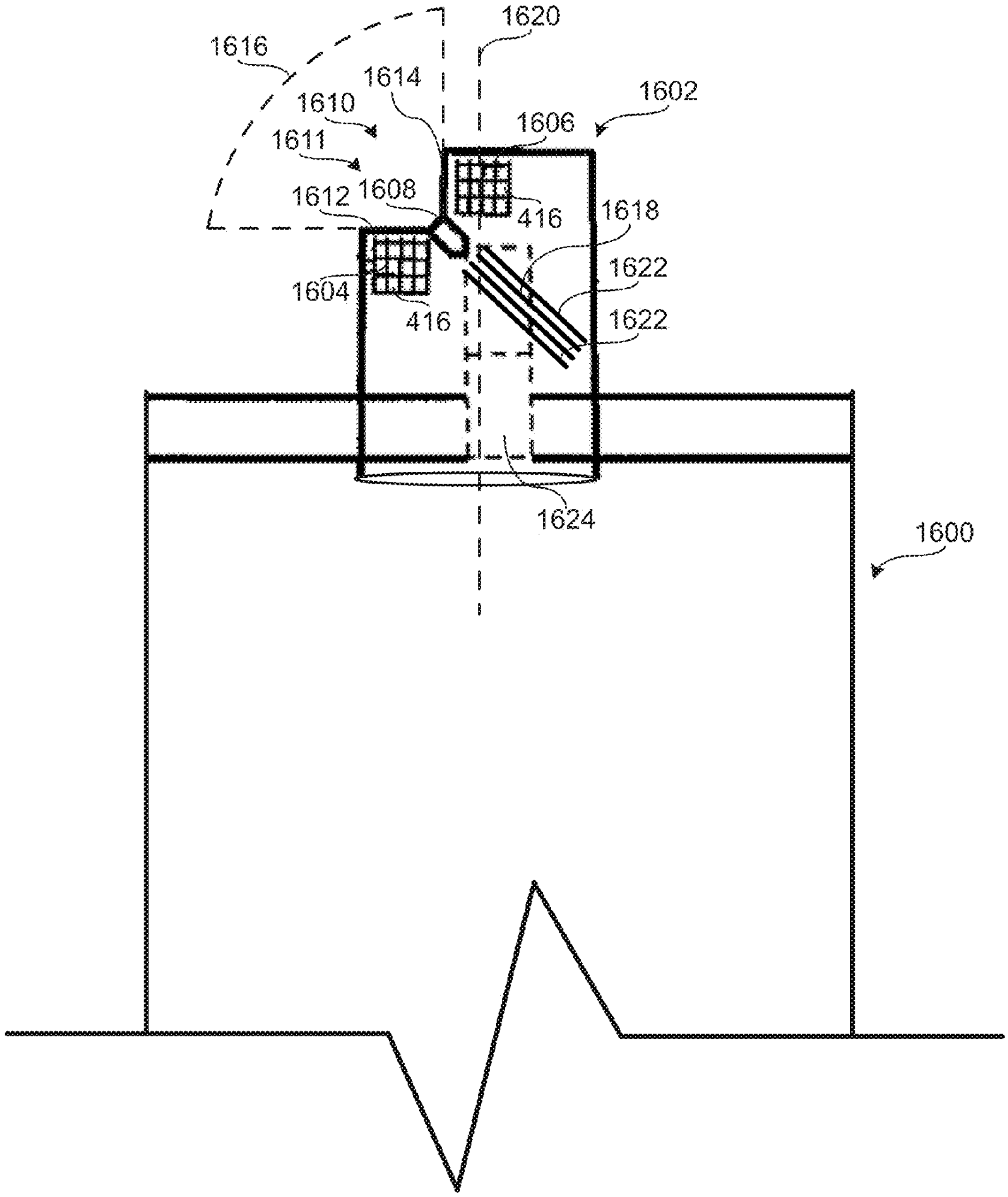
FIG. 16 depicts another example tab.

FIG. 16 depicts a container 1600 coupled to an example tab 1602, via for example, RF sealing or any other suitable method. The example tab 1602 is substantially similar to the example tab 402 of FIG. 4 and may be used to implement at least a portion of any of the examples described herein. The example tab 1602 includes a first grip tab 1604 and a second grip tab 1606 between which a tear initiation area or point 1608 is positioned. A notch 1610 is positioned at a corner 1611 of the example tab 1602 and between the grip tabs 1604 and 1606 to focus a force (e.g., a shear force) applied by a person, as discussed above, to the tear initiation area or point 1608. The grip tabs 1604 and 1606 include respective first and second edges 1612 and 1614 that define the notch 1610 having an angle 1616 of approximately ninety degrees. Additionally, the example tab 1602 may include a tear seal 1618 positioned at an angle relative to a longitudinal axis 1620 of the example tab 1602 and between a plurality of guides, reinforcing features or extrusions 1622. While not shown, the tear seal 1618 may include tapered portions (not shown) similar to the tapered portions 426 (FIG. 4) and 428 (FIG. 4) of the example tab 402 of FIG. 4.

As discussed above, in operation, a person may grasp the first grip tab 1604 with one hand and the second grip tab 1606 with the other hand and then apply a first force in a first direction to the first grip tab 1604 and a second force in a second direction, opposite the first direction, to the second grip tab 1606, such that a shear movement initiates a tear (not shown) adjacent or proximate the tear initiation area 1608. Once the tear is initiated, the person may continue to apply the first force in the first direction to the first grip tab 1604 and the second force in the second direction to the second grip tab 1606, thereby propagating the tear along, for example, the tear seal 1618 and/or between the guides 1622 to enable access to a membrane port or tube 1624. The example tab 1602 may be produced and/or fabricated using a similar process as discussed above. As such, a description will not be repeated here.

Figure 17:
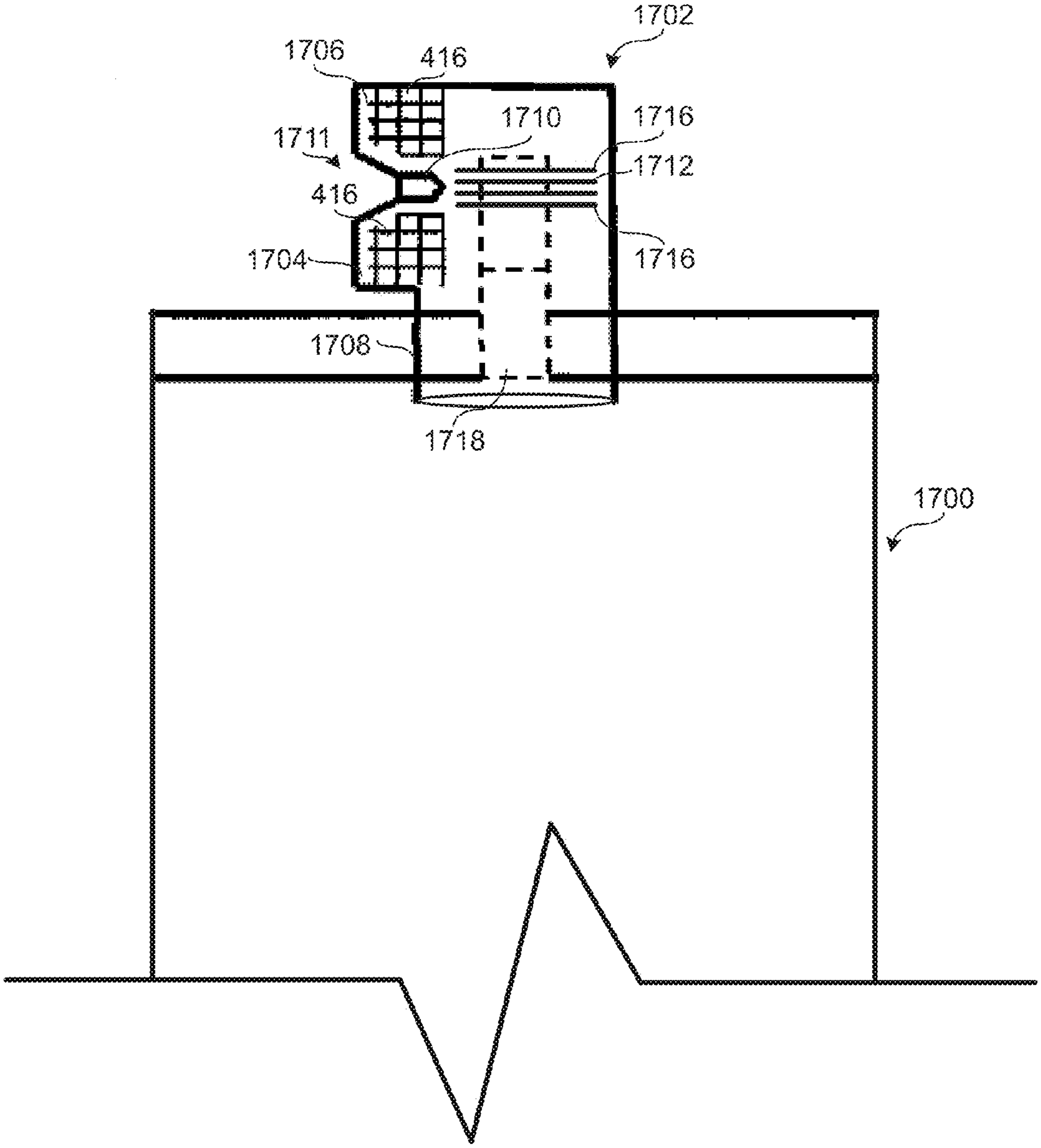
FIG. 17 depicts another example tab.

FIG. 17 depicts a container 1700 coupled to an example tab 1702 via, for example, RF sealing or any other suitable method. The example tab 1702 is substantially similar to the example tab 402 of FIG. 4 and may be used to implement at least a portion of any of the examples described herein. However, in contrast, the example tab 1702 includes a first grip tab 1704 and a second grip tab 1706 both of which are positioned adjacent a side 1708 of the example tab 1702. A tear initiation area or point 1710 is positioned between the grip tabs 1704 and 1706 and proximate a notch 1711. Additionally, the example tab 1702 may include a tear seal 1712 substantially perpendicularly positioned relative to a longitudinal axis 1714 of the example tab 1702 and between a plurality of guides, reinforcing features or extrusions 1716. While not shown, the tear seal 1712 may include tapered portions (not shown) similar to the tapered portions 426 (FIG. 4) and 428 (FIG. 4) of the example tab 402 of FIG. 4.

As discussed above, in operation, a person may grasp the first grip tab 1704 with one hand and the second grip tab 1706 with the other hand and then apply a first force in a first direction to the first grip tab 1704 and a second force in a second direction, opposite the first direction, to the second grip tab 1706, such that a shear movement initiates a tear (not shown) adjacent or proximate the tear initiation area 1710. Once the tear is initiated, the person may continue to apply the first force in the first direction to the first grip tab 1704 and the second force in the second direction to the second grip tab 1706, thereby propagating the tear along, for example, the tear seal 1712 and/or between the guides 1716 to enable access to a membrane port or tube 1718. The example tab 1702 may be produced and/or fabricated using a similar process as discussed above. As such, a description will not be repeated here.

Figure 18:
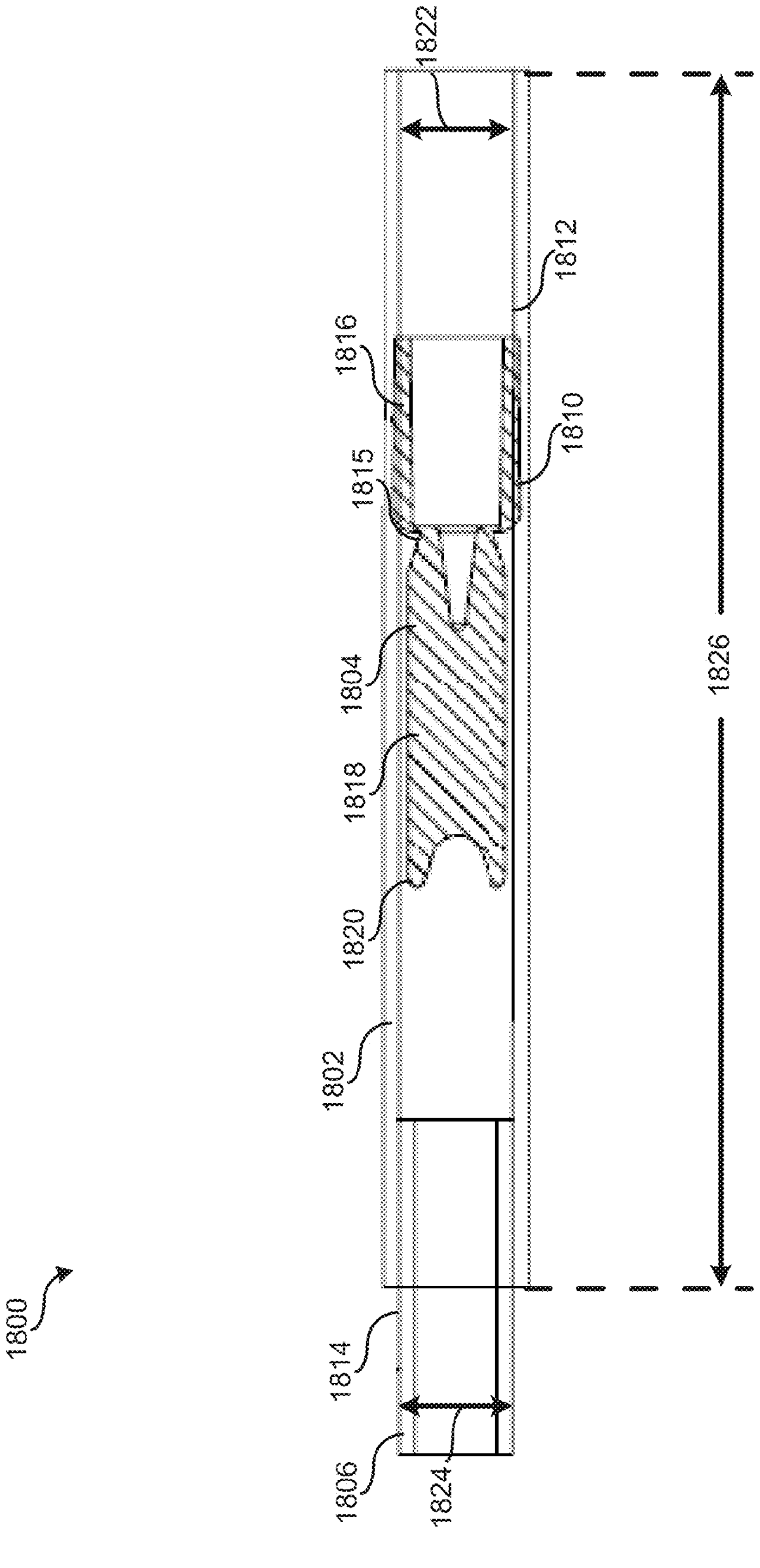
FIG. 18 depicts an example frangible assembly.

FIG. 18 depicts a frangible assembly 1800 that may be used to implement at least a portion of the examples described herein. The frangible assembly 1800 includes a frangible housing 1802, a frangible 1804 that is positioned in the frangible housing 1802 and a bushing 1806 that partially extends from the frangible housing 1802. An outer surface 1810 of the frangible is coupled to an inner surface 1812 of the frangible housing 1802 and, similarly, a portion of an outer surface 1814 of the bushing 1806 is coupled to the inner surface 1812 of the frangible housing 1802. When the frangible 1804 is intact within the frangible housing 1802, the frangible 1804 substantially prevents fluid flow through the frangible housing 1802. To enable fluid flow through the frangible housing 1802, the frangible 1804 is broken along a frangible joint 1815 to separate a port 1816 of the frangible 1804 from an elongated member 1818 of the frangible 1804. Once the frangible 1804 is separated, the elongated member 1818 may move away from the port 1816 until an end 1820 of the elongated member 1818 engages the bushing 1806. In this example, the frangible housing 1802 is a substantially straight tube made of polyvinyl chloride, for example, having an inner diameter 1822 that is substantially consistent throughout and corresponds to an outer diameter 1824 of the bushing 1806. Thus, because the frangible housing 1802 is a substantially straight tube, a length 1826 of and/or an area within the frangible housing 1802 may be easily tailored to a particular application and/or to enable the frangible 1804 to be more easily broken and/or to more effectively separate once broken within the frangible housing 1802.

Figure 19:
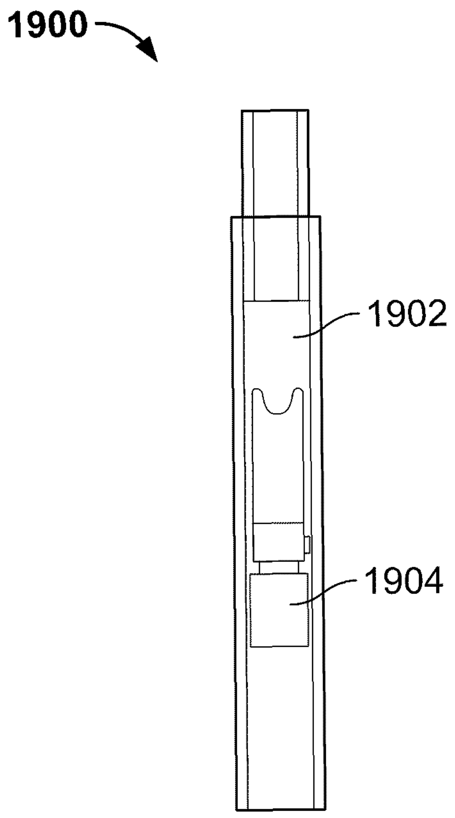
FIG. 19 depicts another example frangible assembly.

FIG. 19 depicts a frangible assembly 1900 that is similar to the frangible assembly 1800 of FIG. 18 and may be used to implement at least a portion of the examples described herein. The frangible assembly 1900 includes a frangible housing 1902 and a frangible 1904 that is positioned in the frangible housing 1902.

Figure 20:
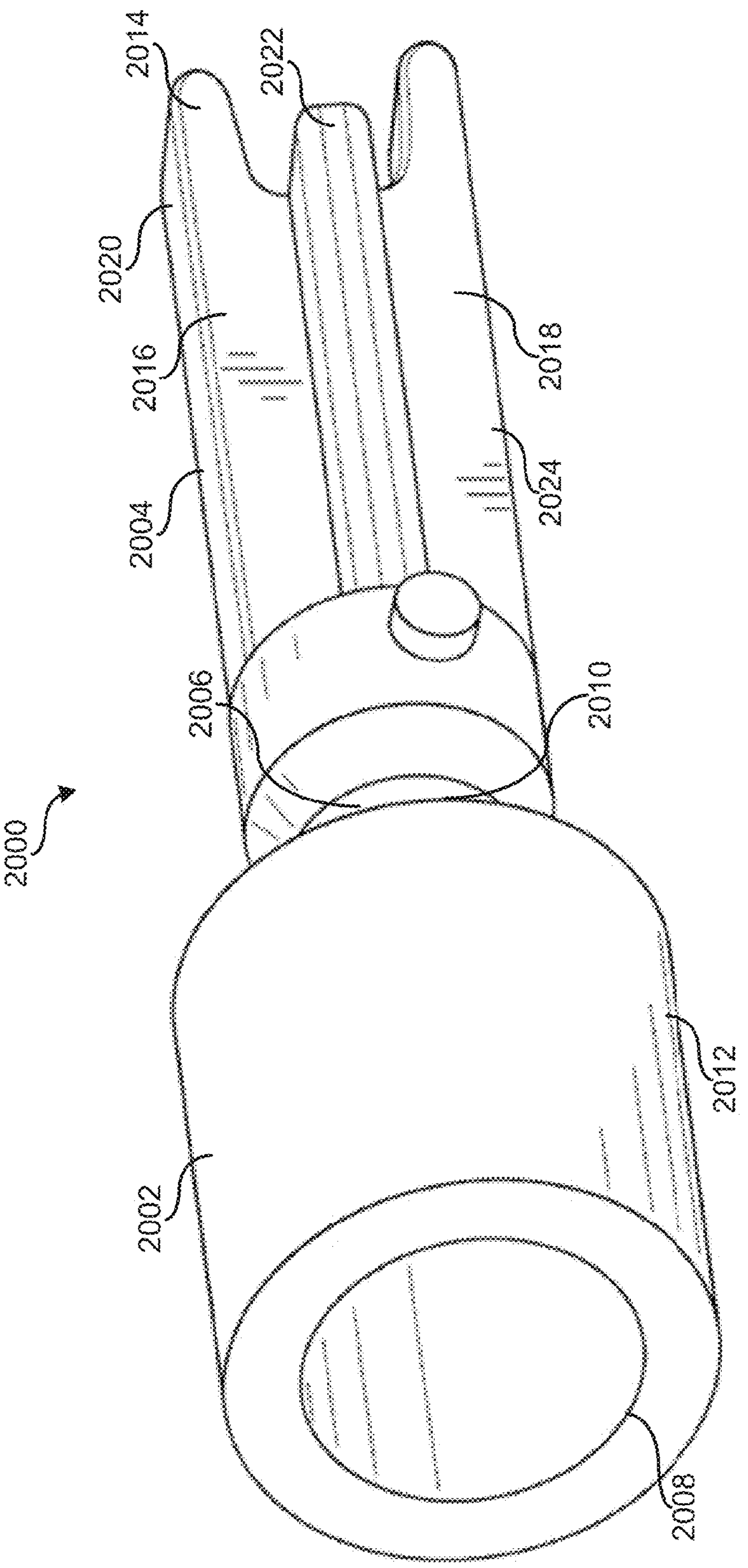
FIG. 20 depicts an example frangible.

FIG. 20 depicts a frangible 2000 that includes a port 2002 and an elongated member 2004 between which a frangible joint 2006 is positioned. The frangible 2000 may be made of any suitable material such as, for example, a polycarbonate material. The port 2002 defines a cavity 2008 that enables fluid to flow though the port 2002 once the elongated member 2004 is broken along the frangible joint 2006. However, when the frangible joint 2006 is intact, a position of an end 2010 of the elongated member 2004 relative to the cavity 2008 of the port 2002 substantially prevents fluid flow through the port 2002. In practice, the frangible 2000 may be positioned within a frangible housing (e.g., a tube) (not shown) and a surface 2012 of the port 2002 may be coupled to an inner surface (not shown) of the frangible housing to prevent fluid from flowing between the inner surface of the frangible housing and the surface 2012 of the port 2002. The frangible housing may be made of any suitable material such as, for example, polyvinyl chloride, and may be a contrasting color (e.g., green) to enable a person to be able to readily identify when the frangible 2000 has been separated and to substantially ensure adequate or optimal flow through the frangible 2000.

To break the frangible 2000 along the frangible joint 2006 to enable fluid flow through the port 2002 and, thus, the frangible housing, a person may grasp the port 2002 with one hand and the elongated member 2004 with the other hand and apply a force to the frangible joint 2006, thereby breaking the frangible 2000 along the frangible joint 2006 and separating the port 2002 from the elongated member 2004. Once separated, the elongated member 2004 may move away from the port 2002 within the frangible housing until an end 2014 of the elongated member 2004 engages a shoulder or bushing (not shown) of the frangible housing, for example, thereby stopping further movement of the elongated member 2004 away from the port 2002. Separating the port 2002 from the elongated member 2004 along the frangible joint 2006 enables fluid to flow through the port 2002 and about channels, two of which are represented by reference numbers 2016 and 2018, defined by radial extensions, three of which are represented by reference numbers 2020, 2022 and 2024, of the elongated member 2004 within the frangible housing.

Figure 21:
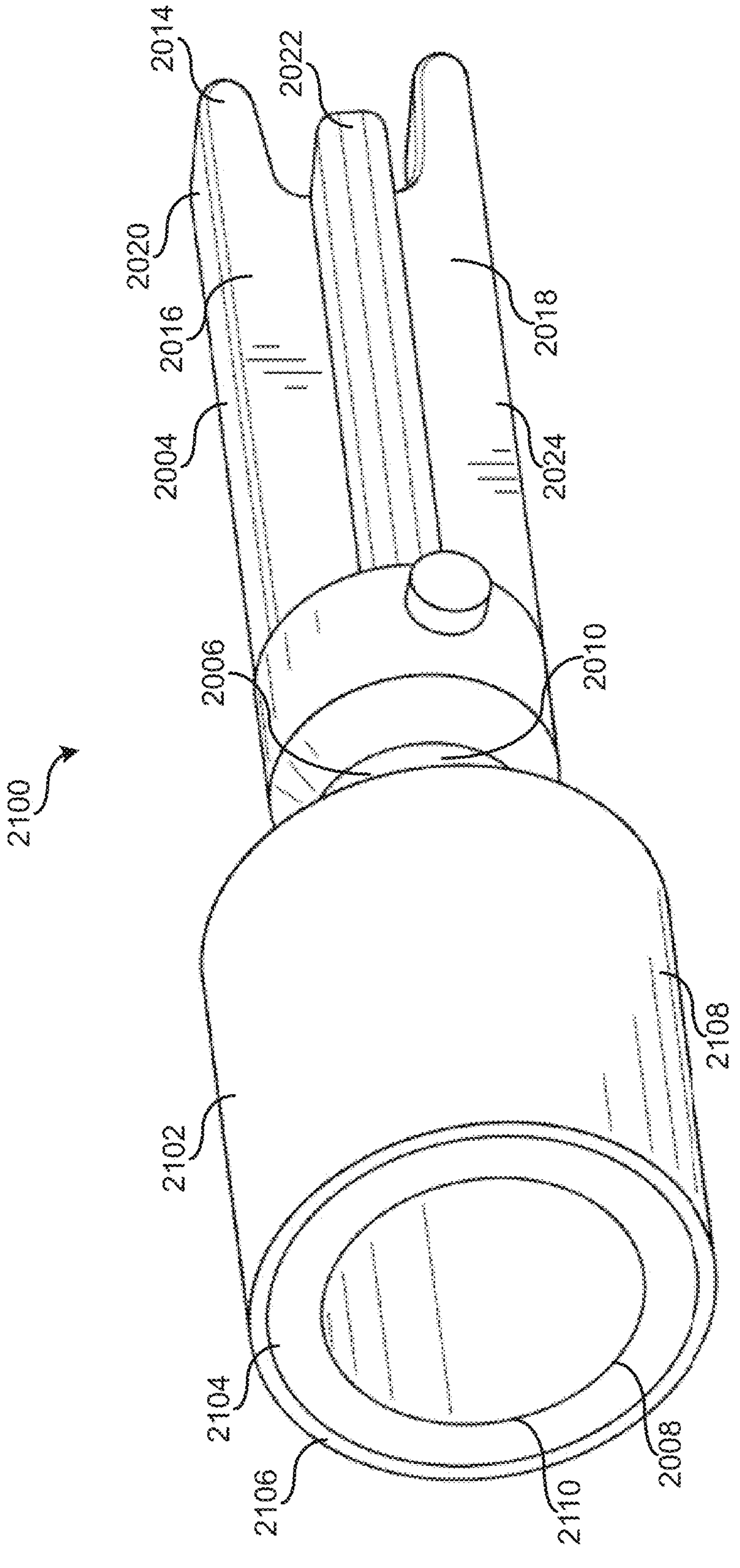
FIG. 21 depicts another example frangible.

FIG. 21 depicts a frangible 2100 that is similar to the frangible 2000 of FIG. 20. However, the frangible 2100 includes a port 2102 having a first portion 2104 and a second portion 2106. The frangible 2100 may be produced such that a first portion 2104 is a polypropylene material and a second portion 2106 is a Hytrel® material (e.g., thermoplastic polyester elastomers) or any other suitable material that may thermally adhere to the first portion 2104 and be solvent bondable to polyvinyl chloride, for example. In such examples, after the molding process and positioning within frangible housing (not shown), a frangible assembly (not shown) that includes the frangible 2100 and the frangible housing, may be autoclaved at approximately one hundred twenty one degrees Celsius for approximately one hour. After the frangible assembly is autoclaved, the frangible assembly may be leak tested by pressurizing the frangible assembly via, for example, air.

Results in which the frangible assembly was leak tested indicated that the frangible assembly can withstand at least a pressure of approximately six pounds per square inch. Specifically, the position of the frangible 2100 within the frangible housing substantially prevented leakage between a surface 2108 and the inner surface of the frangible housing via the coupling between the surface 2108 and the inner surface of the frangible housing. Additionally or alternatively, if the frangible 2100 is made of a polypropylene material, the frangible 2100 may be treated to substantially prevent the formation of a living hinge that may have a tendency to form when breaking the frangible 2100 along the frangible joint 2006. In some examples, the treatment may include exposing the frangible 2100 to gamma irradiation, ultraviolet light, electron beam, etc., or adding an additive to the polypropylene such as, for example, polyethylene, polyester elastomer, styrene, ethylene vinyl acetate, etc.

In some examples, the first portion 2104 may be a polypropylene material and the second portion 2106 may be a Hytrel® material, the material(s) described in U.S. Pat. No. 4,327,726 or any other suitable material that may thermally adhere to the first portion 2104 and be solvent bondable to polyvinyl chloride, for example. In examples in which the first and second portions 2104 and 2106 are made of different materials, the port 2102 may be made using a molding process (e.g., an over molding process or a multi-component molding process) that may include two-steps in which the first material is allowed to at least partially cool prior to the second material being injected, for example.

In other examples, the first and second portions 2104 and 2106 may both be made of a polypropylene material. However, the second portion 2106 may have been altered by exposure to a chemical (e.g., a strong acid, nitric acid, sulfuric acid) while the first portion 2104 may have not been exposed to the chemical. Generally, exposing the second portion 2106 to the chemical causes reactions on the surface 2108 of the second portion 2106, thereby enabling the second portion 2106 to be solvent bondable to polyvinyl chloride even though the port 2102 is made of the polypropylene material.

In other examples, the first and second portions 2104 and 2106 may both be made of a polypropylene material. However, the second portion 2106 may have been exposed to a plasma surface treatment while the first portion 2104 may not have been exposed to the plasma surface treatment. The plasma surface treatment may include exposing the second portion 2106 to ionized gasses, which causes reactions on the surface 2108 of the second portion 2106. In other examples, the plasma surface treatment may include exposing the second portion 2106 to ionized air that at least partially oxidizes the surface 2108 and causes the surface 2108 to become more hydrophilic and, thus, compatible (e.g., solvent bondable) with polyvinyl chloride. Additionally or alternatively, the plasma surface treatment may form hydroxyl groups on the surface 2108. These hydroxyl groups or other functional groups may be reactable with other materials (e.g., coupling agents, silanes, titanates, UV adhesives) to further modify the surface 2108, enabling the second portion 2106 to be solvent bondable to polyvinyl chloride. The coupling agents may have organic groups that are compatible with polyvinyl chloride. In examples in which the coupling agent is a UV adhesive, exposing the coupling agent to ultraviolet light may crosslink a UV bond between the polypropylene material and the adjacent polyvinyl chloride material.

In some examples, the first portion 2104 may be a polypropylene material and the second portion 2106 may be an additive (e.g., waxes, copolyester, acrylic, styrene, styrene copolymers, ethylene vinyl acetate, etc.) added to the polypropylene material which, during processing, moves toward (e.g., blooms to) the surface 2108 and, thus, modifies the surface 2108. The additive enables the polypropylene to be solvent bondable to polyvinyl chloride. Additionally, the additive may have a relatively low molecular weight, thereby enabling migration of the additive in relatively high shear conditions.

While the second portion 2106 of the port 2102 surrounds the first portion 2104 in the example frangible 2100 of FIG. 21, the first portion 2104 may instead surround the second portion 2106. In such examples, a tube (not shown) may be positioned adjacent and coupled to a surface 2110 of the port 2102.

FIG. 22 is a table 2200 that depicts results obtained from leak testing different frangible assemblies having frangibles made of different materials. In this example, the frangible assemblies were leak tested at different pressures for a ten second hold time. However, besides the testing conducted at approximately twenty five pounds per square inch (psi), the frangible assemblies were not flexed prior to leak testing. The different frangibles were made of a polypropylene homopolymer, a polypropylene copolymer, a treated polypropylene homopolymer and a treated polypropylene copolymer. Results in which "OK" appears represents that substantially no leakage occurred between the frangible and the frangible housing, and results in which "Leak" appears represents that leakage occurred between the frangible and the frangible housing. Column 2202 depicts the test conducted on each of the different types of frangible assemblies and columns 2204-2216 depict the results obtained from the respective tests. As shown in the table 2200, the results indicate that less leakage occurred when the frangibles were made of polypropylene copolymer as compared to when the frangibles were made of polypropylene homopolymer. The frangibles made of the polypropylene homopolymer material and the frangibles made of the polypropylene copolymer material were produced having a standard head type, a line speed of approximately 75 FPM, a gap of approximately 0.25 inches, an initial Dyne level of between about 31 and 32 and a final Dyne level of approximately 70.

Figure 23:
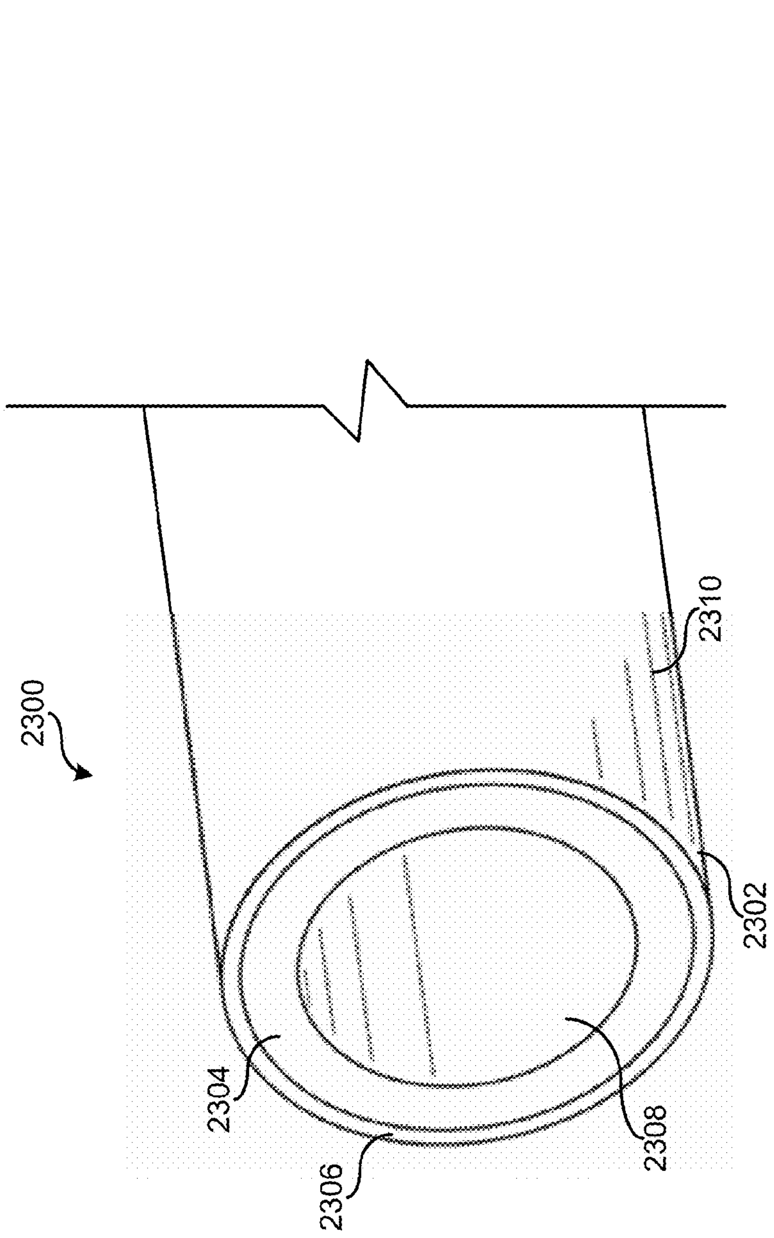
FIG. 23 depicts an example port.

FIG. 23 depicts a port 2300 for use with medical apparatus having a body 2302 that includes a first portion 2304 and a second portion (e.g., a monomolecular layer, a substantially monomolecular layer) 2306. The body 2302 defines a cavity 2308 through which fluid may flow. In practice, a tube (not shown) or a frangible housing (not shown) may be positioned around and coupled to a surface 2310 of the port 2300. In some examples, the port 2300 may be used to implement the example port 2102 of the example frangible 2100 of FIG. 21.

Figure 24:
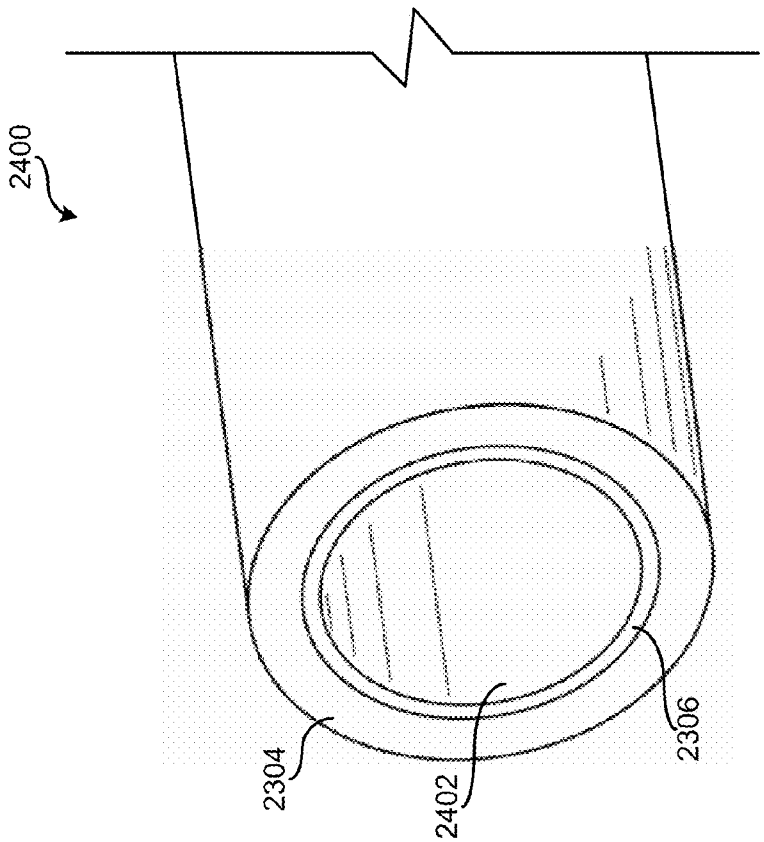
FIG. 24 depicts another example port.

FIG. 24 depicts a port 2400 for use with medical apparatus that is substantially similar to the example port 2300. However, the first portion 2304 of the port 2400 surrounds the second portion 2306 as opposed to the second portion 2306 surrounding the first portion 2304. In practice, a tube (not shown) may be positioned adjacent and coupled to a surface 2402 of the port 2400.

Figure 25:
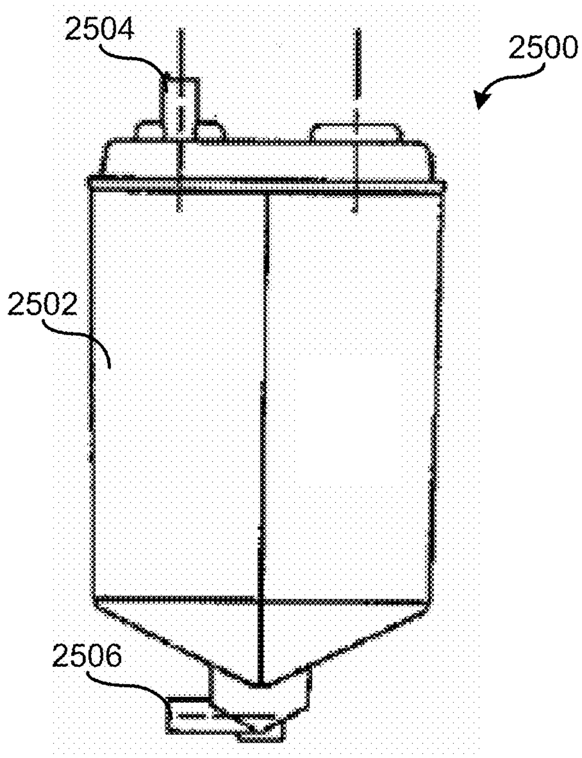
FIGS. 25 and 26 depict an example filter housing.
Figure 26:
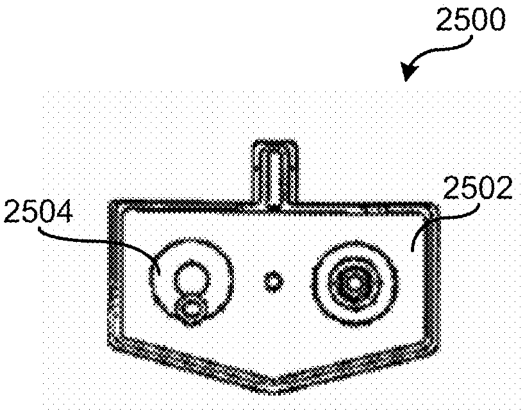

FIGS. 25 and 26 depict different views of an example reservoir housing 2500 that may be used in the medical field. The reservoir housing 2500 includes a body 2502 and first and second ports 2504 and 506. The first port 2504 may be substantially similar to either the port 2300 of FIG. 23 or the port 2400 of FIG. 24 and the second port 2506 may be similar or different from the first port 2504. The second port 2506 may be substantially similar to either the port 2300 of FIG. 23 or the port 2400 of FIG. 24.

In practice, the reservoir housing 2500 may be used to house different fluids (e.g., blood, a blood component, a preservative solution, etc.) that may enter the reservoir housing 2500 via the first port 2504 and may exit the reservoir housing 2500 via the second port 2506.

Figure 27:
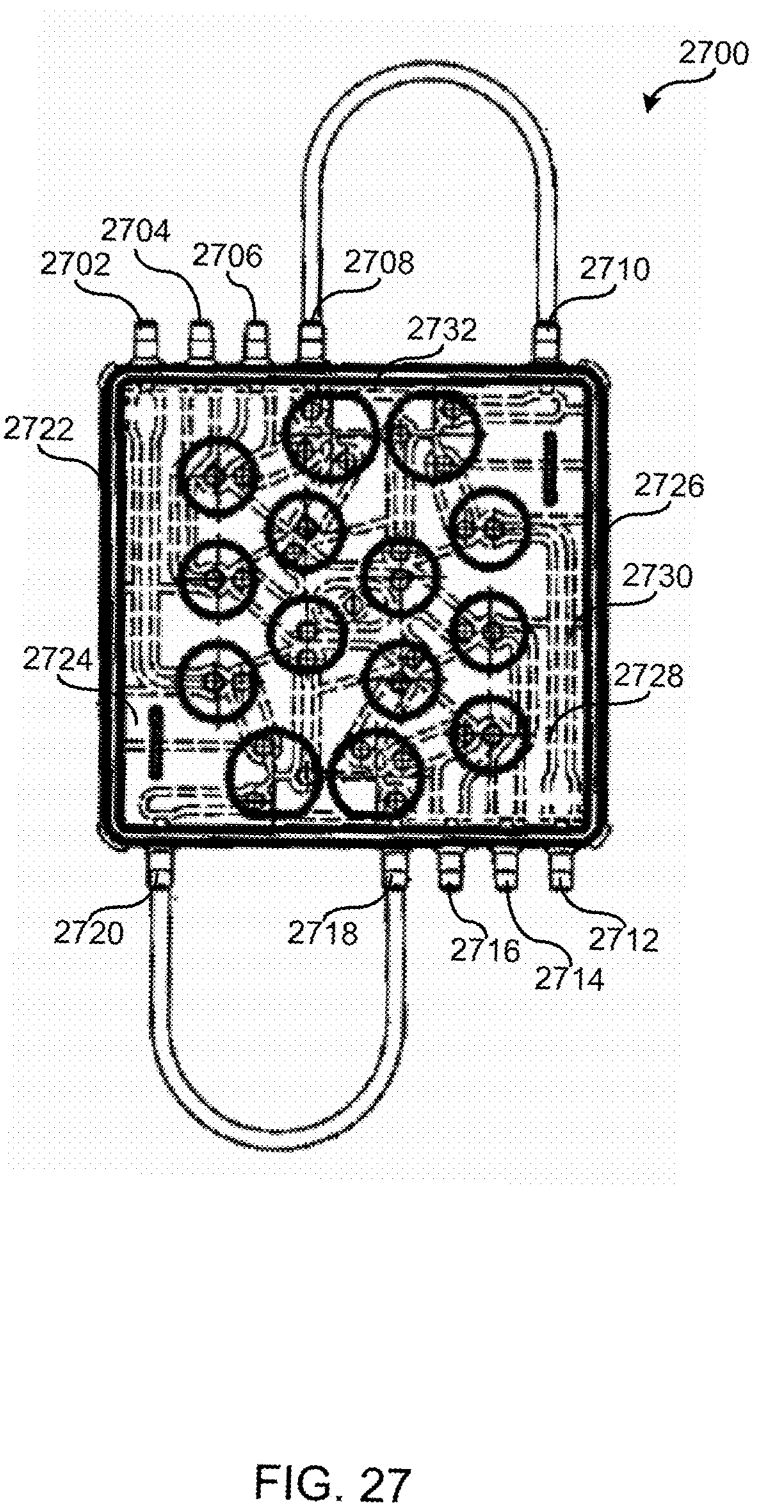
FIG. 27 depicts an example cassette.

FIG. 27 depicts a cassette 2700 that may be used, for example, in blood processing procedures. The cassette 2700 includes a plurality of ports 2702-2720 to enable fluid to flow into or out of the cassette 2700 and/or to enable fluid to flow to and from different portions of the cassette 2700. Additionally, the cassette 2700 includes a body 2722 to which flexible diaphragms, one of which is represented by reference number 2724, are sealed at least along a peripheral edge 2726 of the body 2702 on either side of the cassette 2700. In practice, the cassette 2700 may be positioned in a housing (not shown) of a blood processing device (not shown). To move fluid, for example, within cavities 2728, 2730 and 2732 of the cassette 2700, pressure (e.g., positive pressure and/or negative pressure) is exerted against the cassette 2700, thereby moving the flexible diaphragms and pumping the fluid through the cassette 2700.

Figure 28:
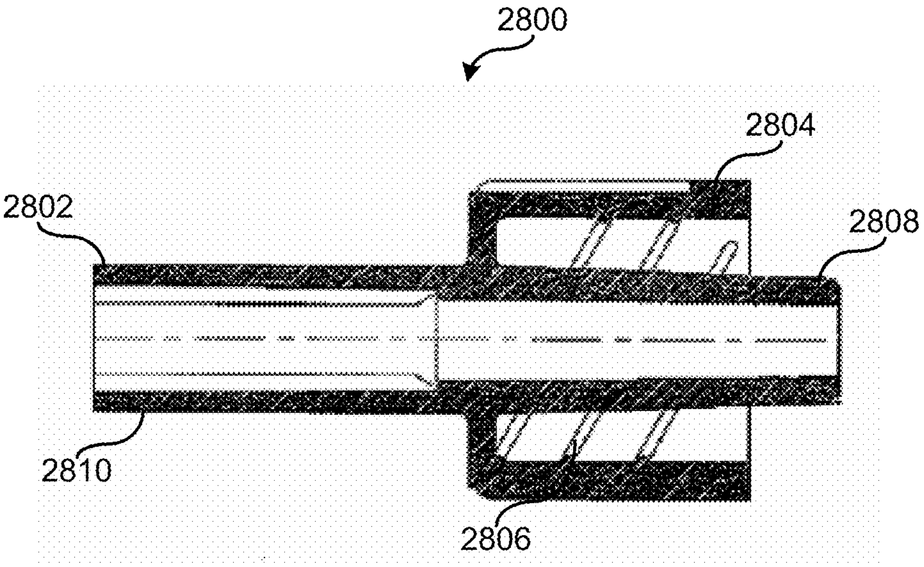
FIG. 28 depicts an example threaded luer.

FIG. 28 depicts a threaded luer or luer (e.g., a threaded male luer component) 2800 that may be used in the medical industry. The luer 2800 includes a port or rigid tube 2802 and a connector 2804 having internal threads 2806 that surrounds a tubular portion 2808. The port 2802 may be substantially similar to the port 2300 of FIG. 23 or the port 2400 of FIG. 24. In practice, a tube (not shown) may surround and be coupled to a surface 2810 of the port 2802 and, for example, a female luer component (not shown) may be threaded into the internal threads 2806 such that the female luer component is at least partially positioned between the connector 2804 and the tubular portion 2808.

Figure 29:
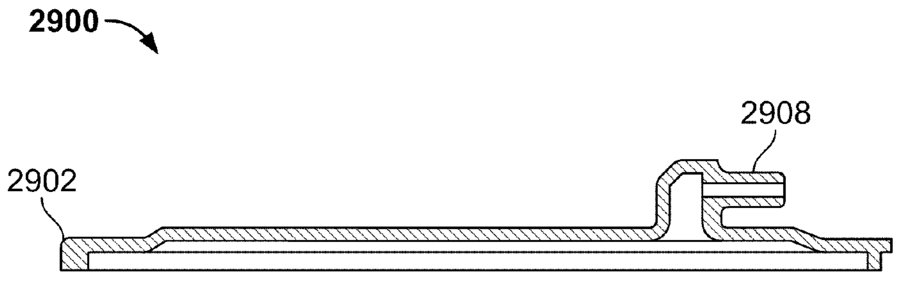
FIGS. 29 and 30 depict an example filter housing.
Figure 30:
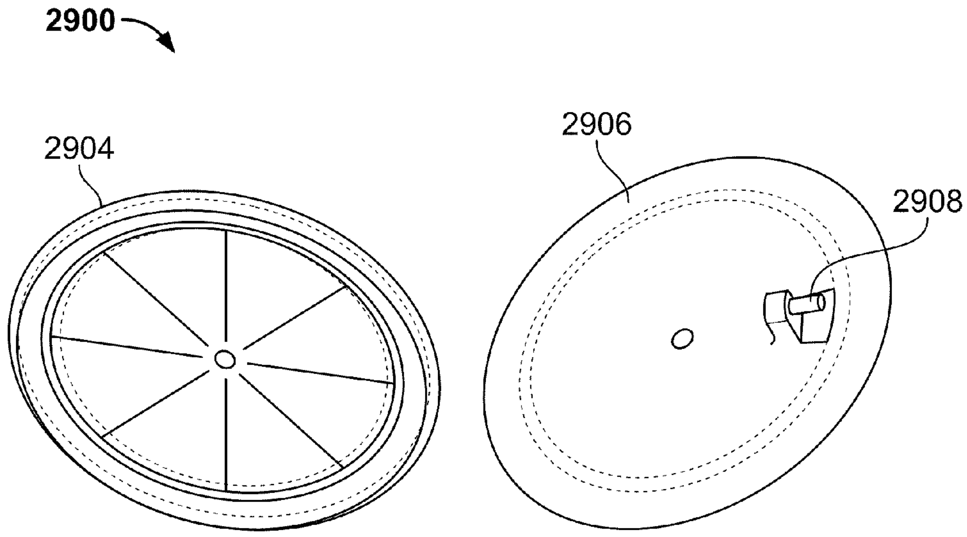

FIGS. 29 and 30 depict different views of an example filter housing 2900 that can be used in the medical industry. The filter housing 2900 includes a body 2902 that includes a first portion 2904 that may be removably coupled to a second portion 2906. In this example, the second portion 2906 includes a port 2908 that may be substantially similar to the port 2300 of FIG. 23 or the port 2400 of FIG. 24.

Figure 31:
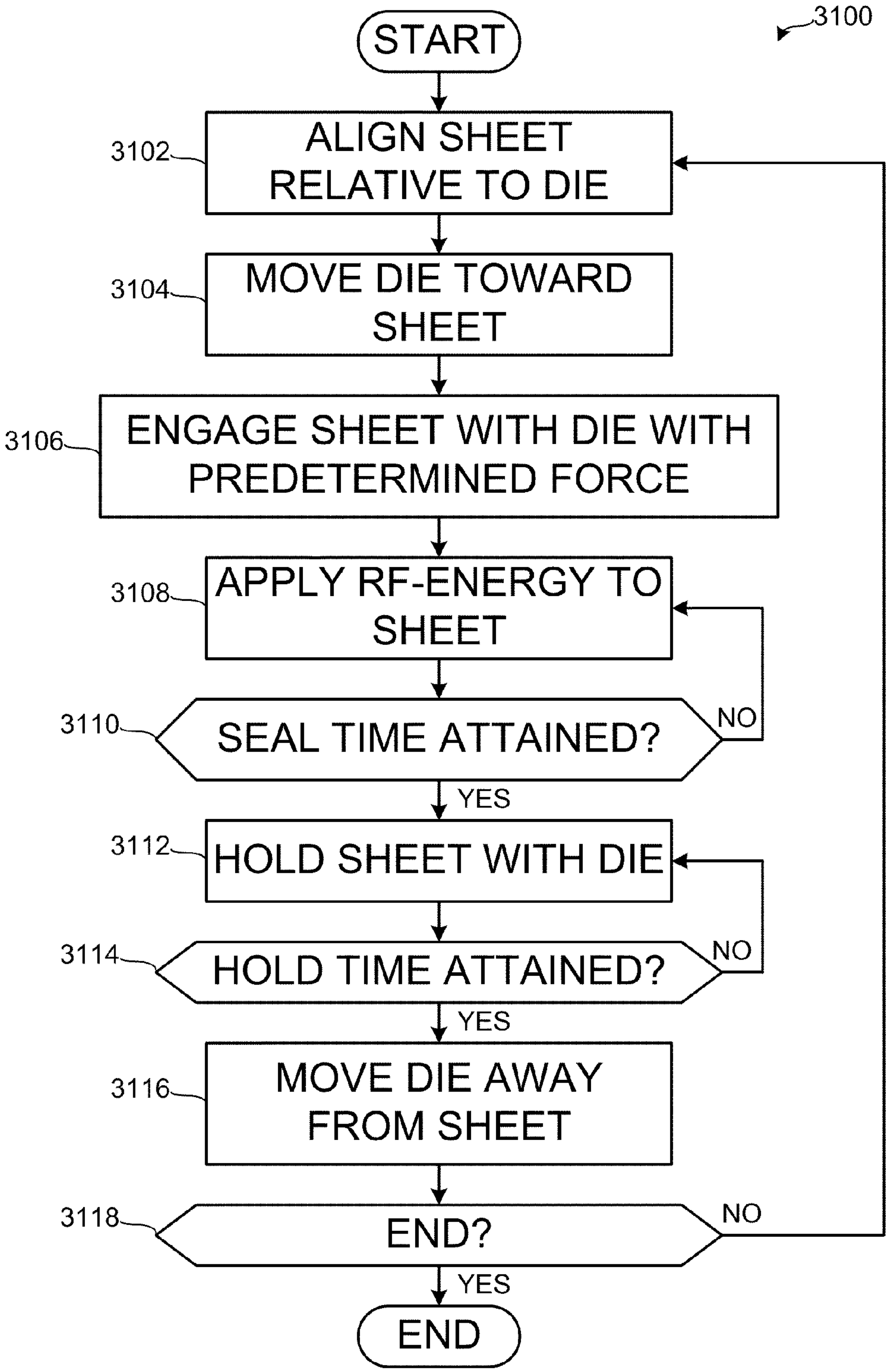
FIGS. 31-33 are flow diagrams representative of example processes that may be performed to produce the examples described herein.
Figure 32:
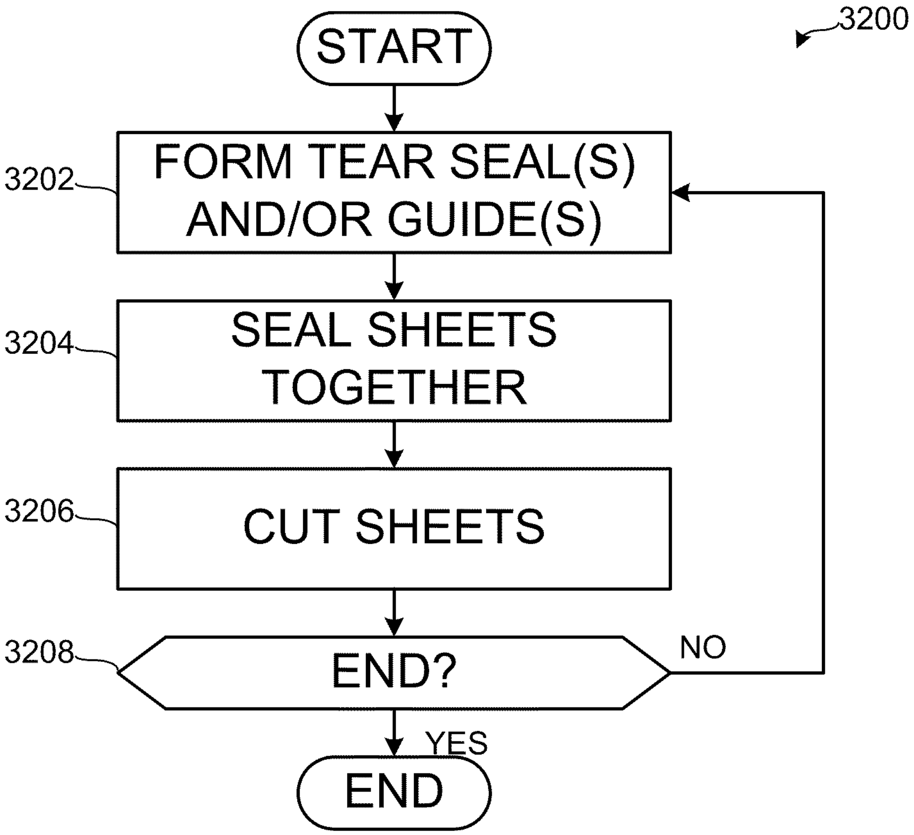
Figure 33:
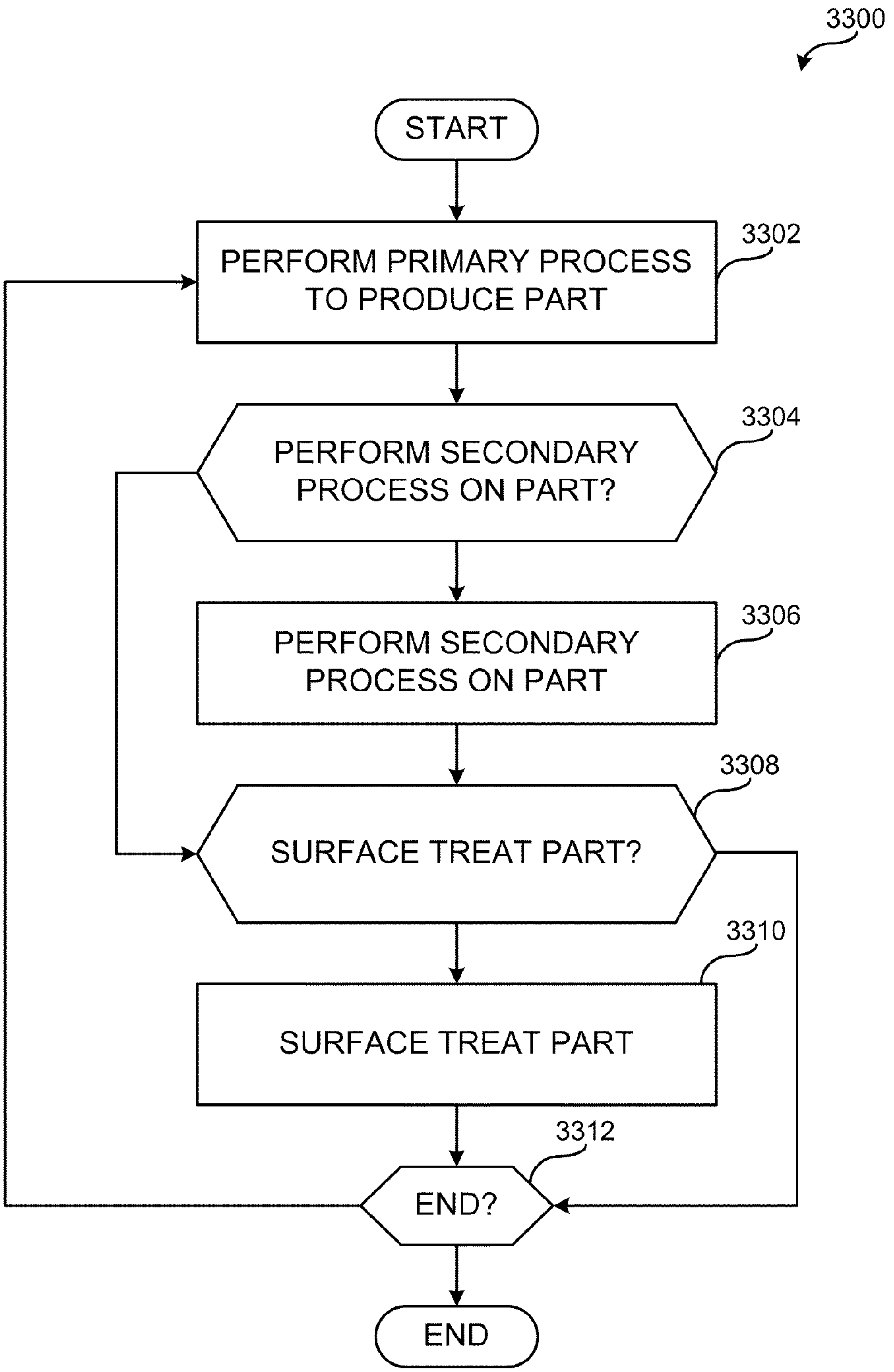

FIGS. 31-33 depicts flow diagrams that are representative of processes or methods that can be performed to produce the example apparatus described herein. In particular, FIG. 31 depicts a flow diagram representative of operations that may be performed to produce, for example, the example tear seals and/or the example guides described herein; FIG. 32 depicts a flow diagram representative of operations that may be performed to produce, for example, the example tear seals, the example guides and/or example tabs described herein; and FIG. 33 depicts a flow diagram representative of operations that may be performed to produce, for example, the example ports described herein. Further, although the example operations of FIGS. 31-33 are described with reference to the flow diagrams of FIG. 31-33 other methods of implementing the example methods may be employed. For example, the order of execution of the blocks may be changed, and/or some of the blocks described may be changed, eliminated, sub-divided, or combined.

FIG. 31 depicts an example method 1400 that may used to produce and/or fabricate example tear seals and/or the example guides. To do so, in some examples, initially, a sheet is aligned relative to a die (block 3102) on, for example, a surface (not shown) beneath the die. The die is then moved (e.g., lowered) toward the sheet (block 3104) until the die engages the sheet with a predetermined force (block 3106) and/or a predetermined die gap is attained. An RF-generator (not shown) communicatively coupled to the die then applies RF-energy to the sheet via the die (block 3108). In some examples, the RF-energy may melt a portion of the sheet, which then flows toward and extrudes into one or more of the plurality of grooves defined by the die, thereby forming the tear seal and/or the example guides.

The example method 3100 then determines whether or not a seal time has been attained (block 3110) such as, for example, three seconds. If the example method 3100 determines that the seal time has not been attained control returns to block 3108. However, if the example method 3100 determines that the seal time has been attained, control advances to block 3112. The RF-energy is then no longer applied to the sheet but the die may hold (e.g., remain engaged to and/or adjacent) the sheet (block 3112) for a hold time to enable, for example, the melted portion of the sheet to set. The example method 3100 then determines whether or not the hold time has been attained (block 3114) such as, for example, five seconds. If the example method 3100 determines that the hold time has not been attained, control returns to block 3112. However, if the example method 3100 determines that the hold time has been attained control advances to block 3116. The die is then moved away from the sheet (block 3116) and the example method 3100 determines whether it should align another sheet relative to the die (block 3118). Otherwise the example method 3100 of FIG. 31 is ended.

FIG. 32 depicts an example method 3200 that may used to produce and/or fabricate example tear seals, example guides and/or example tabs. Initially, the example method 3200 forms the tear seal and/or the guides (block 3202) on, for example, a first sheet and a second sheet, as discussed above in connection with the method 3100 of FIG. 31. The sheets may then be sealed together (block 3104) to form, for example, the shape of the example tab and/or a medical container having the example tab. Additionally, in some example, sealing the sheets together may form grip tabs, a plurality of projections, a notch and/or a tear initiation area. The sheets may be sealed together using any suitable methods such as, RF sealing, heat sealing, etc.

The example method 3200 then may cut the tab (block 3206) from the surrounding sheeting via a die-cut assembly (not shown) once the sheets are sealed together. However, to eliminate subsequent die cutting operations, a tear seal die (not shown) may be used to seal the sheets together as well as to cut and/or separate the tab from the surrounding sheeting once the sheets are sealed together. The example method 3200 then determines whether it should form the tear seal, the example guides and/or the example tab. Otherwise the example method 3200 of FIG. 32 is ended.

Turning to FIG. 33, a process is performed to produce a part (block 3302) such as, for example, a port, etc. In some examples, the part may be produced by molding the part of polypropylene. The polypropylene may be any suitable type of polypropylene such as, for example, a normal molecular weight polypropylene or a relatively low molecular weight polypropylene. In examples in which the polypropylene has a relatively low molecular weight, the part may be formed using a material width melt flow rate of greater than 10 g/min (American Society for Testing and Materials (ASTM) D1238, condition L) and a notched Izod of less than 0.5 (ASTM D256A). In practice, the lower molecular weight polypropylene may decrease the likelihood that a living hinge will form when breaking, for example, the frangible. Additionally or alternatively, as discussed above, the part may be produced using an over molding process.

However, in other examples, the part may be produced by molding the part of polypropylene and an additive. As discussed above, the additive (e.g., waxes, copolyester, acrylic, styrene, styrene copolymers, ethylene vinyl acetate, etc.), may be added to the polypropylene material during processing to modify the surface of the part, thereby enabling the part to be solvent bondable to polyvinyl chloride. Additionally or alternatively, the additive (e.g., incompatible polymers, compatible polymers, inorganic particulate, polyethylene, polyester elastomer, styrene, ethylene vinyl acetate, etc.) may be added to the polypropylene material during processing to modify the part, thereby decreasing the likelihood that a living hinge will form when breaking, for example, the frangible.

The example method 3300 then determines whether or not to perform a secondary process on the part (block 3304). If the example method 3300 determines to perform a secondary process, control advances to block 3306. However, if the method 3300 determines not to perform the secondary process, control advances to block 3308. In some examples, the secondary process may include exposing the part to ionizing radiation such as, for example, gamma rays, electron beams, ultraviolet light, etc. Additionally or alternatively, the secondary process may include exposing the part to chemicals such as, for example, acid (e.g., relatively strong acid, nitric acid, sulfuric acid) and/or exposing the part to ionizing plasma such as, for example, ionized gas. As described above, the secondary processes may enable the part to be solvent bondable to polyvinyl chloride and/or decrease the likelihood that a living hinge will form when breaking, for example, the frangible.

The method 3300 then determines whether or not to surface treat the part (block 3308). If the example method 3300 determines to surface treat the part, control advances to block 3310. However, if the method 3300 determines not to surface treat the part, control advances to block 3312. In some examples, the surface treatment may include applying a coupling agent to the surface of the part such as, for example, titanates, silanes, etc. to further modify the surface of the part to enable the part to be solvent bondable to polyvinyl chloride. The method 3300 then determines whether or not to again perform the primary process to produce a part 3312. Otherwise, the method 3300 of FIG. 33 is ended. Once the part is produced, the part may be utilized in producing any of the apparatus described herein.

Figure 34:
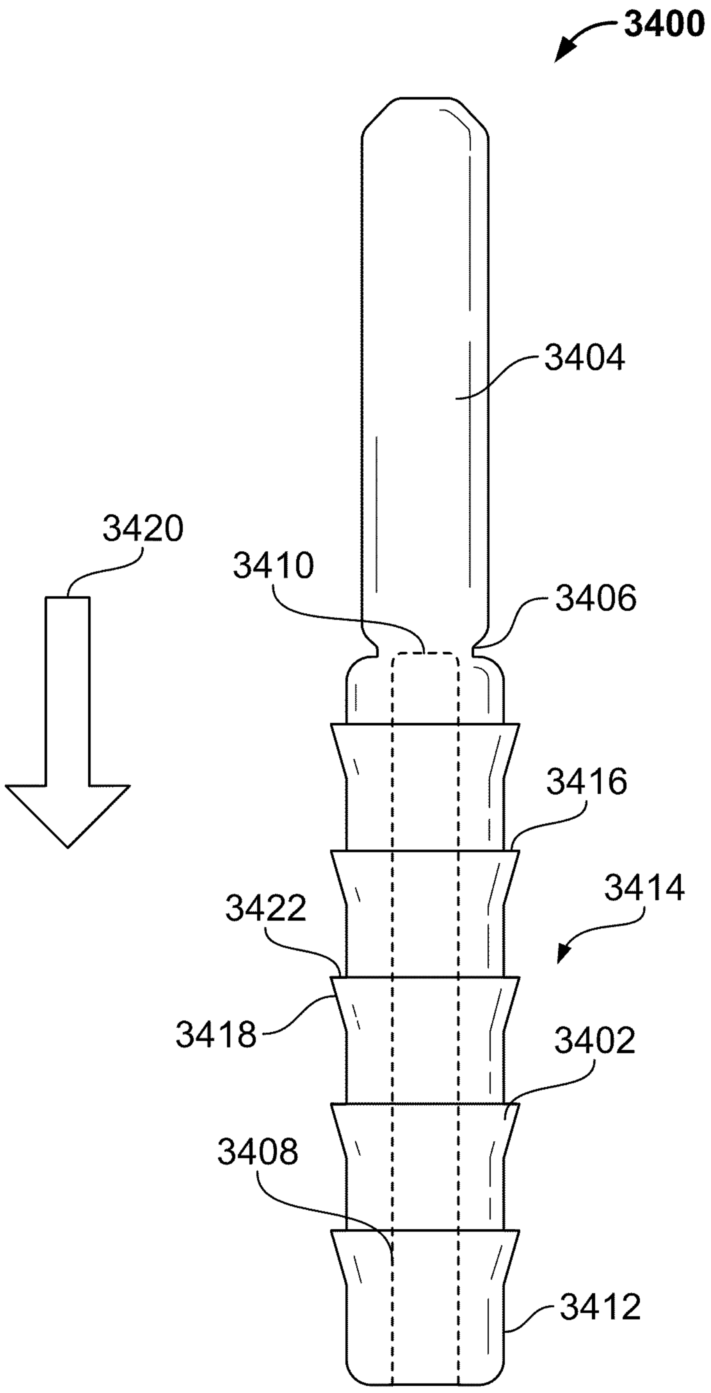
FIG. 34 depicts an example frangible.

FIG. 34 depicts an example frangible 3400. The frangible includes a port 3402 and a breakable cannula or elongated body 3404 between which a frangible joint 3406 is positioned. In some examples, the frangible 3400 may be made of a polycarbonate material. The port 3402 defines a cavity 3408 that enables fluid flow therethrough once the elongated member 3404 is broken along the frangible joint 3406. However, when the frangible joint 3406 is intact, as depicted, a position of an end 3410 of the elongated member 3404 relative to the cavity 3408 substantially prevents fluid flow through the port 3402.

In some examples, an exterior surface 3412 includes an example surface structure or locking mechanism 3414 to at least partially facilitate coupling (e.g., mechanical coupling) with a bushing or tube (not shown) made of a thermally expandable material. The thermally expandable material may be solvent bondable to PVC. In some examples, the locking mechanism 3414 includes a plurality of circumferential spikes 3416 that may have a triangular shape. The spikes 3416 may include a tapered surface 3418 to facilitate entry into a tube or bushing in a direction generally indicated by arrow 3420, for example. The spikes 3418 may include another surface 3422 that may extend substantially perpendicularly from the exterior surface 1312 to substantially prevent the frangible 3400 from being moved within the bushing or tube in a direction generally opposite that indicated by arrow 3420 once the frangible 3400 is positioned in the bushing or tube.

Figure 35:
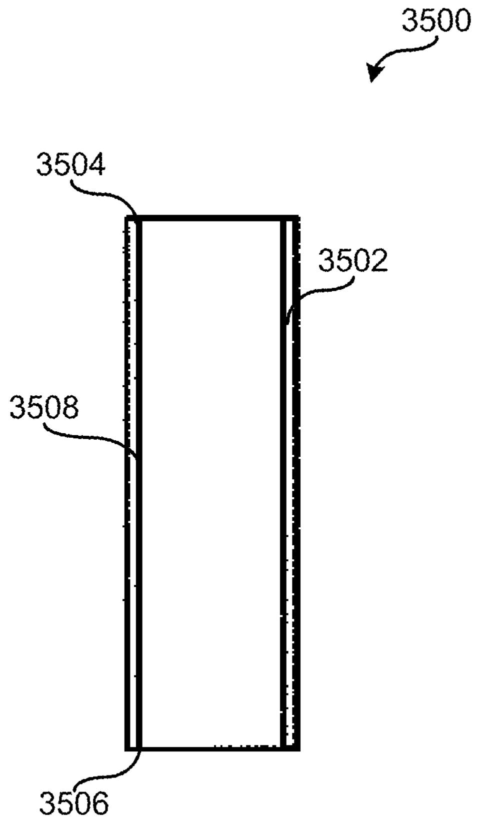
FIG. 35 depicts an example cylindrical tube.

FIG. 35 depicts a cylindrical tube, bushing or second material 3500 that may be made of a thermal expandable material. In some examples, the thermal expandable material may be and/or include Plastisol. However, any other material or substance having thermal expandable characteristics may be used instead. The tube 3500 may include a body 3502 defining opposing openings 3504 and 3506 and a chamber 3508. In some examples, the openings 3504 and 3506 and/or the chamber 3508 may be sized to enable the port 3402 to be at least partially positioned within the chamber 3508.

Figure 36:
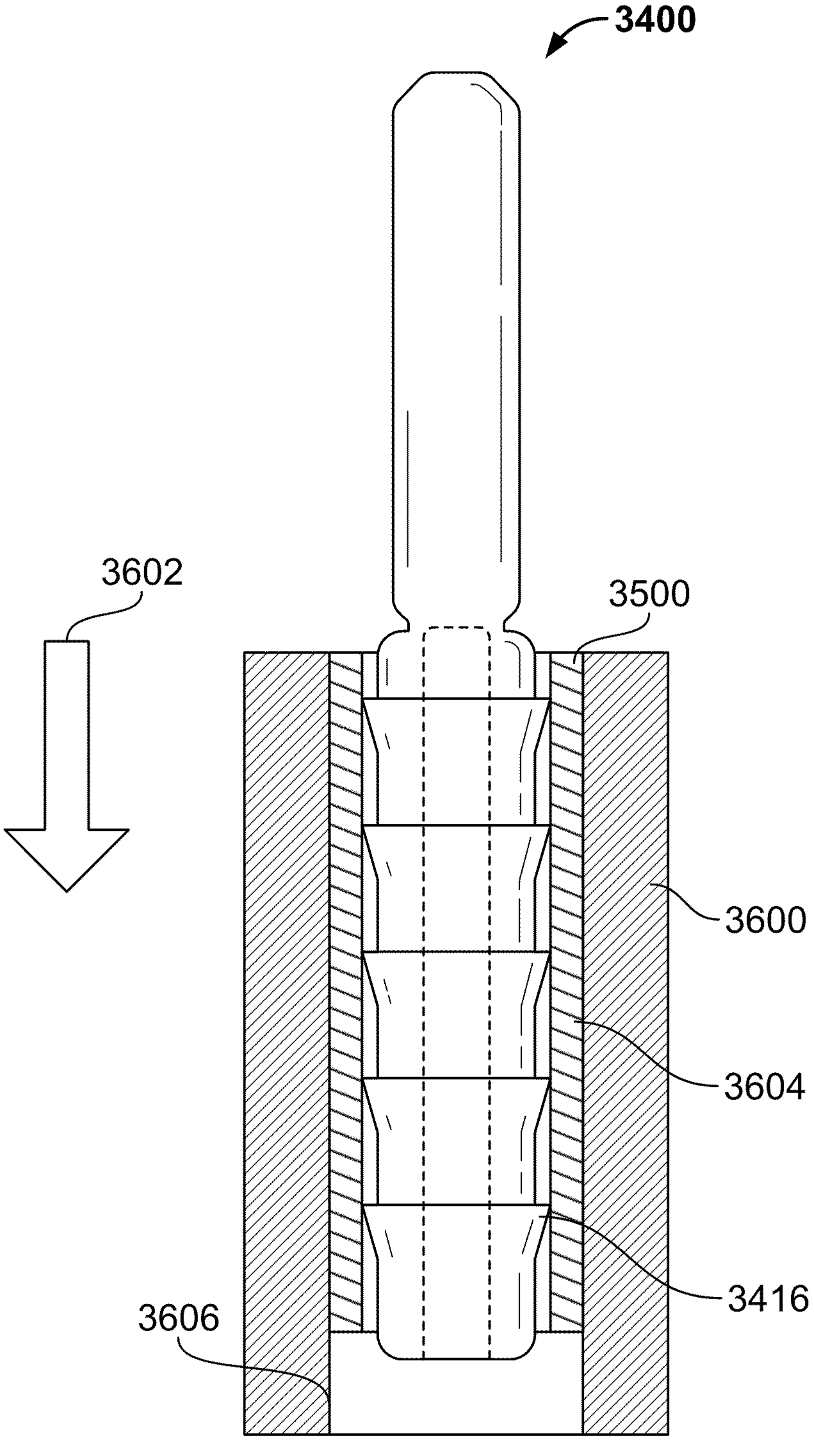
FIG. 36 depicts an example frangible and an example tube positioned in an example housing.

FIG. 36 depicts the frangible 3400 and the tube 3500 positioned in a housing or bushing 3600. In some examples, the housing 3600 may be made of a PVC material, the frangible 3400 may be made of a polypropylene material and the tube 3500 may be made of a thermally expandable material.

In practice, the frangible 3400 may be inserted into the tube 3500 in a direction generally indicated by arrow 3602. As discussed above, the spikes 3416 enable the frangible 3400 to be inserted into the tube 3500 relatively easily in the direction generally indicated by the arrow 3602; however, the spikes 3416 substantially prevent the frangible 3400 from being removed from the tube 3500, once inserted, in a direction generally opposite that of arrow 3602. In other examples, instead of inserting the frangible into the tube 3500, the frangible 3400 may be coated with a thermal expandable material. In such examples, the tube 3500 may be an exterior layer or coating applied to the frangible 3400 as liquid Plastisol.

A coating or adhesive 3604 may then be applied to an exterior surface 3606 of the tube 3500 or to the Plastisol coating on the frangible 3400, for example. In some examples, the coating 3604 may be Cyclohexanone.

The frangible 3400 and the tube 3500 including the coating 3604 may then be inserted into the housing 3600. In some examples, the coating 3604 at least partially enables bonding (e.g., chemical bonding, solvent bonding) to occur between the tube 3500 and the housing 3600. Thus, the tube 3500 may be solvent bondable and/or able to retain a relatively high surface energy, for example.

Figure 37:
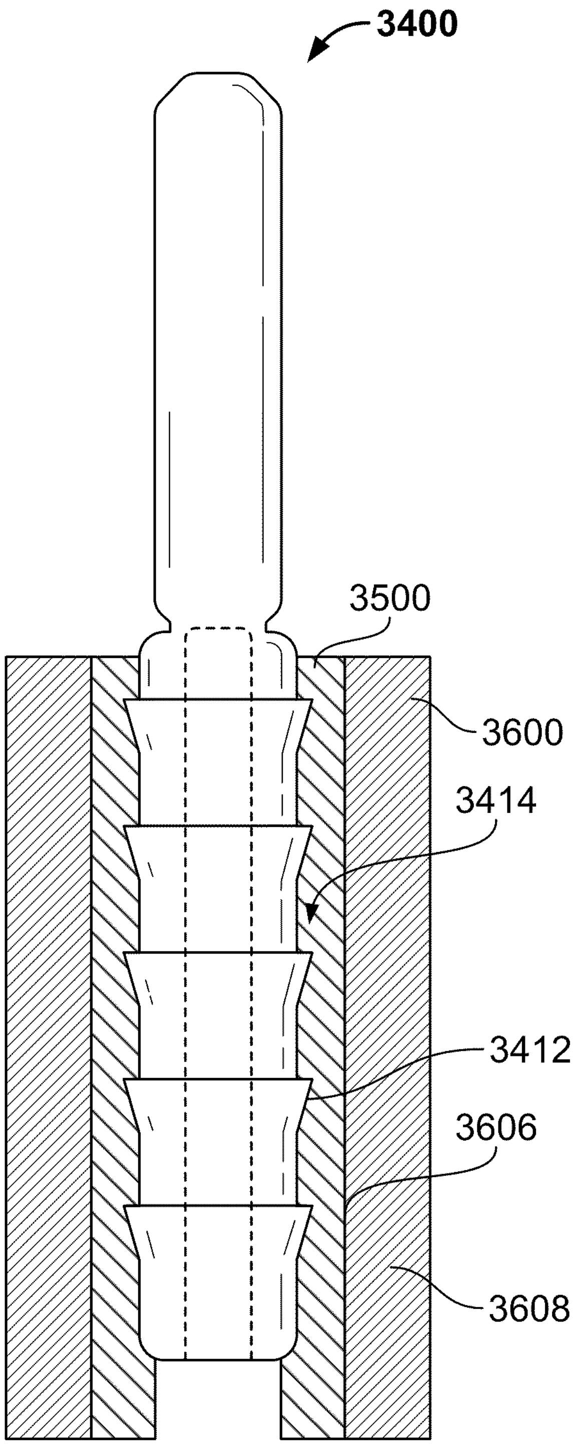
FIG. 37 depicts the example frangible and the example tube coupled in the example housing.

After the coating 3604 has cured, the frangible 3400, the tube 3500 including the coating 3604 and the housing 3600 may be heated. In some examples, the frangible 3400, the tube 3500 including the coating 3604 and the housing 3600 may be heated using steam sterilization. When the tube 3500 is at an expansion temperature, the tube 3500 will expand impressing itself into the spikes 3404 of the frangible 3400. Thus, a mechanical coupling is created between the frangible 3400 and the thermal expandable material (e.g., the tube 3500, the coating, etc.). As indicated in FIG. 37, the mechanical coupling (e.g., the interaction between the expanded tube 3500 and the spikes 3416) between the frangible 3400 and the tube 3500 creates a seal (e.g., an air tight seal) between the exterior surface 3412 of the frangible 3400 and the thermal expandable material (e.g., the tube 3500, the coating, etc.). The chemical bonding between the thermal expandable material and the housing 3600 creates a seal (e.g., an air tight seal) between an interior surface 3608 of the housing 3600 and the exterior surface 3606 of the tube 3500, for example. In other examples, the mechanical coupling between the frangible 3400 and the tube 3500 may be initiated and/or accomplished prior to the insertion into and/or chemical bonding with the housing 3600.

Figure 38:
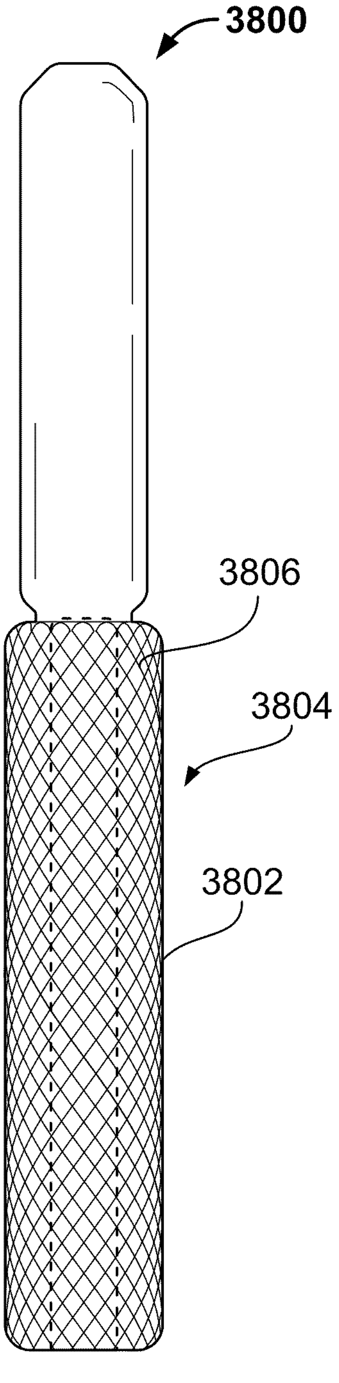
FIGS. 38-41 depict different example frangibles.

FIG. 38 depicts an example frangible 3800 that may be used similarly as the frangible 3400 described above. The frangible 3800 includes an exterior surface 3802 that includes a surface structure or locking mechanism 3804. In some examples, the locking mechanism 3804 may include a diamond shaped pattern 3806. However, any other pattern may be used instead such as, triangles, squares, rectangles, circles, ovals, etc.

Figure 39:
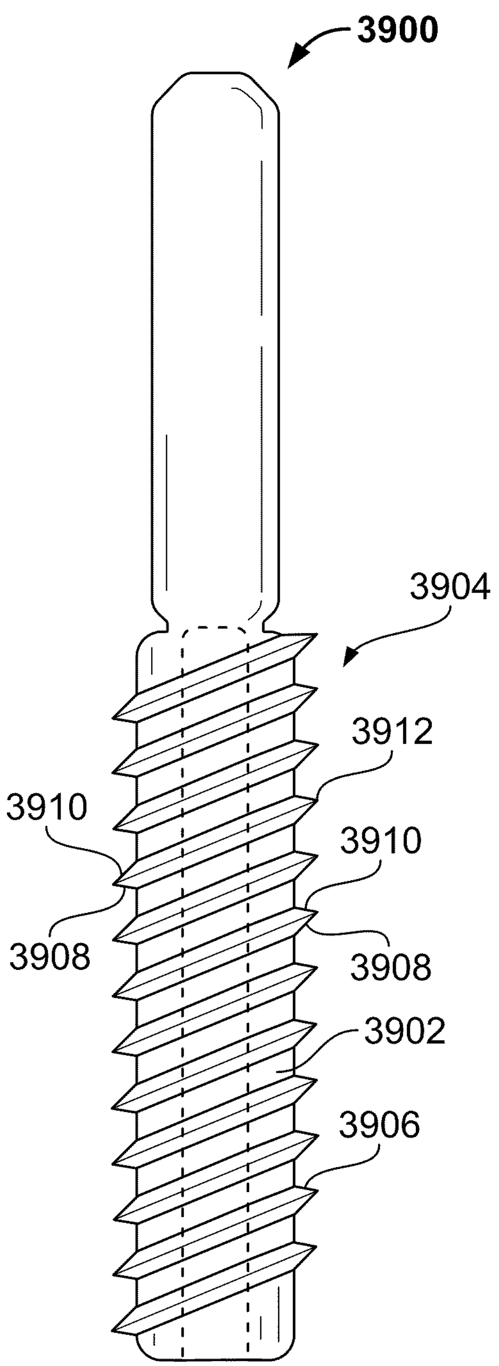

FIG. 39 depicts an example frangible 3900 that may be used similarly as the frangible 3400 described above. The frangible 3900 includes an exterior surface 3902 that includes a surface structure or locking mechanism 3904. In some examples, the locking mechanism 3904 may include helical threads 3906. In some examples, the threads 3906 may include tapered surfaces 3908 and 3910 that come to a point or edge 3912.

Figure 40:
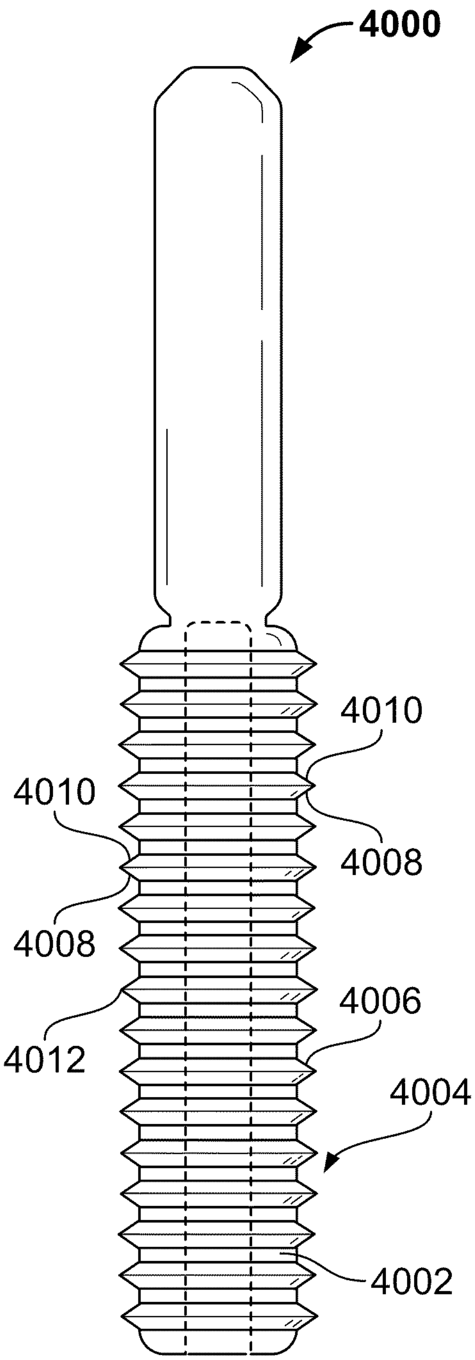

FIG. 40 depicts an example frangible 4000 that may be used similarly as the frangible 3400 described above. The frangible 4000 includes an exterior surface 4002 that includes a surface structure or locking mechanism 4004. In some examples, the locking mechanism 4004 may include circumferential projections or rings 4006. In some examples, the projections 4006 may include tapered surfaces 4008 and 4010 that come to a point or edge 4012.

Figure 41:
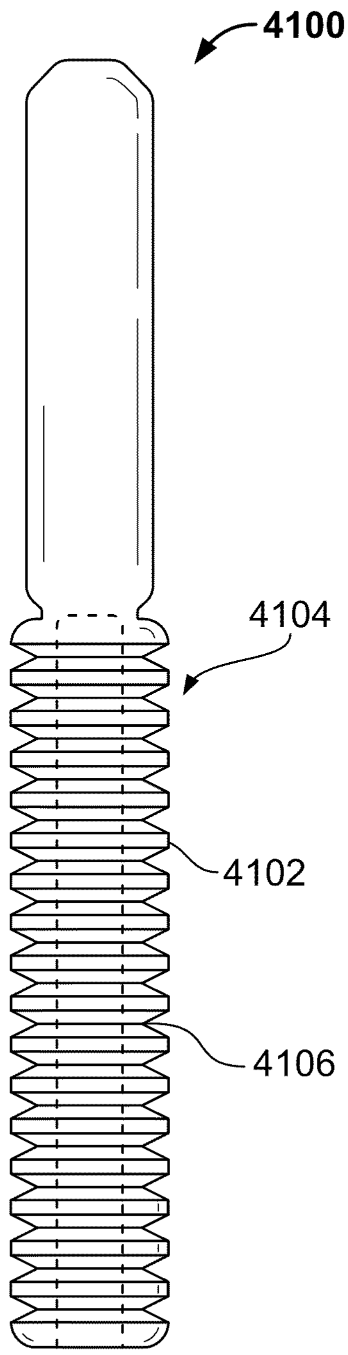

FIG. 41 depicts an example frangible 4100 that may be used similarly as the frangible 3400 described above. The frangible 4100 includes an exterior surface 4102 that includes a surface structure or locking mechanism 4104. In some examples, the locking mechanism 4104 may include circumferential grooves or slots 4106. In some examples, the grooves 4106 may be triangular in shape; however, in other examples, the grooves 4106 may be defined by one or more curved surfaces or a plurality of surfaces (e.g., flat surfaces).

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents.

The invention claimed is:

1. A tab for use with a medical container, comprising: opposing sheets sealed to define an open ended chamber into which a port is to be at least partially positioned, wherein the port is to enable access to the medical container; a tear seal defined by each of the opposing sheets; a first guide positioned on a first side of each of the tear seals; and a second guide positioned on a second side of each of the tear seals; a tear initiation area proximate the tear seals; each tear seal further comprising an elongated lateral portion extending from the tear initiation area toward the medical container having a first end and a second end, a first tapered portion and a second tapered portion, wherein the first end of the lateral portion is adjacent the tear initiation area and the second end of the lateral portion is adjacent the first and second tapered portions, wherein the first and second guides are to enable a tear to propagate substantially between the guides and adjacent the tear seals by moving a first portion of the tab in a first direction and a second portion of the tab in a second direction.

2. The tab of claim 1, wherein the first portion comprises a first grip tab having a plurality of first projections and the second portion comprises a second grip tab having a plurality of second projections.

3. The tab of claim 1, further comprising a notch defined between the first and second portions and adjacent the tear initiation area.

4. The tab of claim 1, wherein the tear is to propagate adjacent at least one of the first tapered portion or the second tapered portion to enable the first portion to be spaced-apart from the second portion to enable access to the port.

5. The tab of claim 1, wherein the first and second guides comprise extrusions.

6. The tab of claim 5, wherein the extrusions have a height of approximately 0.016 inches.

7. The tab of claim 1, wherein the tab is integrally coupled to the medical container.

8. A medical container, comprising: a plurality of sheets sealed along a peripheral edge to define a chamber, wherein the peripheral edge defines: a plurality of openings into which ports are positioned to enable access to the chamber; and a plurality apertures each of which is to enable the medical container to be suspended at a different angle relative to a floor to decrease the likelihood that particulate within the chamber affects a flow rate through at least one of the plurality of ports, wherein the plurality of apertures comprise curved ends to decrease stress points adjacent one of the plurality of apertures from which the medical container is suspended.

9. A die to produce tear seals and a plurality of guides adjacent the tear seals on a sheet of material, comprising: a body comprising a plurality of surfaces adjacent a plurality of grooves defined by the body, wherein RF energy is to be applied to the sheet via the die to form a tear seal adjacent each of the plurality of surfaces and to form a guide adjacent each of the plurality of grooves, the plurality of guides is to enable a tear to propagate substantially between the guides and adjacent the tear seals.

10. The die of claim 9, wherein the plurality of grooves comprise a semi-annular shape.

11. The die of claim 9, wherein the plurality of surfaces comprise a substantially flat surface.

12. A port for use with a medical apparatus, comprising: a first material comprising a polypropylene material; and a second material different than the first material, wherein the second material is coupled to the first material and is solvent bondable to polyvinyl chloride.

13. The port of claim 12, wherein the second material comprises a polypropylene material that has been exposed to at least one of a strong acid, nitric acid, or sulfuric acid.

14. The port of claim 12, wherein the second material comprises one or more thermoplastic polyester elastomers thermally adhered to the first material.

15. The port of claim 12, wherein the second material comprises a polypropylene material that has been exposed to a plasma treatment to enable the second material to be hydrophilic.

16. The port of claim 15, wherein the port is to be exposed to at least one of gamma rays, electron beams, or ultraviolet light.

17. The port of claim 12, wherein the second material is to be further exposed to at least one of coupling agents, silanes, titanates, or UV adhesives.

18. The port of claim 12, wherein the second material comprises an additive that blooms to a surface of the port.

19. The port of claim 18, wherein the additive comprises at least one of wax, copolyester, acrylic, styrene copolymer, or ethylene vinyl acetate.

20. The port of claim 12, wherein the second material comprises a substantially monomolecular layer.

21. The port of claim 12, wherein the second material comprises a thermal expandable material.

22. The port of claim 13, wherein the second material comprises Plastisol.

23. The port of claim 13, wherein the first material comprises surface structure to facilitate mechanical coupling with the second material.

* * * * *